(12) United States Patent
Wang et al.

(10) Patent No.: US 12,140,582 B2
(45) Date of Patent: Nov. 12, 2024

(54) MULTIFUNCTIONAL POLYSACCHARIDE-BASED MUD LOGGING BARCODE TRACERS

(71) Applicant: Saudi Arabian Oil Company, Dhahran (SA)

(72) Inventors: Wei Wang, Quincy, MA (US); Sehoon Chang, Boston, MA (US); Hooisweng Ow, Woburn, MA (US)

(73) Assignee: Saudi Arabian Oil Company, Dhahran (SA)

( * ) Notice: Subject to any disclaimer, the term of this patent is extended or adjusted under 35 U.S.C. 154(b) by 159 days.

(21) Appl. No.: 17/522,445

(22) Filed: Nov. 9, 2021

(65) Prior Publication Data

US 2023/0148198 A1    May 11, 2023

(51) Int. Cl.
  *G01N 33/24*      (2006.01)
  *G01N 21/64*      (2006.01)

(52) U.S. Cl.
  CPC ............. *G01N 33/24* (2013.01); *G01N 21/64* (2013.01); *Y10T 436/13* (2015.01)

(58) Field of Classification Search
  CPC ........ Y10T 436/13; G01N 33/24; E21B 47/11
  USPC .......................................................... 436/27
  See application file for complete search history.

(56) References Cited

U.S. PATENT DOCUMENTS

| | | | |
|---|---|---|---|
| 4,772,563 A | 9/1988 | Evangelista et al. | |
| 5,124,268 A | 6/1992 | Dakubu | |
| 5,168,927 A | 12/1992 | Stegenneier | |
| 6,250,848 B1 | 6/2001 | Moridis et al. | |
| 6,590,647 B2 | 7/2003 | Stephenson | |
| 6,691,780 B2 | 2/2004 | Nguyen et al. | |
| 7,032,662 B2 | 4/2006 | Malone | |
| 7,485,471 B1 | 2/2009 | Sun et al. | |
| 7,588,827 B2 | 9/2009 | Nie et al. | |

(Continued)

FOREIGN PATENT DOCUMENTS

| | | |
|---|---|---|
| EP | 0171978 | 11/1990 |
| EP | 1721603 | 11/2006 |

(Continued)

OTHER PUBLICATIONS

Kaewsaneha, C. et al. "Immobilization of fluorescein isothiocyanate on magnetic polymeric nanoparticle using chitosan as spacer," Journal of Colloid and Interface Science 377 (2012) 145-152 (Year: 2012).*

(Continued)

*Primary Examiner* — Jennifer Wecker
*Assistant Examiner* — Michelle Adams
(74) *Attorney, Agent, or Firm* — Fish & Richardson P.C.

(57) ABSTRACT

Compositions and methods for determining the origin location of subterranean rock samples. In some implementations, the compositions include a nanoparticle tag that includes a natural polysaccharide, a fluorescent dye, and superparamagnetic nanoparticles. In some implementations, a method of determining the origin location of a subterranean rock sample includes mixing the nanoparticle tag into a fluid, flowing the fluid into a subterranean formation, recovering subterranean rock samples from the formation, separating tagged rock samples from untagged rock samples using a magnet, and determining the origin location by analyzing a fluorescent signal of the nanoparticle tag.

15 Claims, 31 Drawing Sheets

(56) References Cited

U.S. PATENT DOCUMENTS

| | | |
|---|---|---|
| 7,879,625 B1 | 2/2011 | Boss |
| 8,269,501 B2 | 9/2012 | Schmidt et al. |
| 8,337,783 B2 | 12/2012 | Locascio et al. |
| 8,627,902 B2 | 1/2014 | Hammer |
| 8,638,104 B2 | 1/2014 | Barber et al. |
| 8,877,954 B2 | 11/2014 | Giesenberg et al. |
| 9,080,097 B2 | 7/2015 | Gupta et al. |
| 9,133,709 B2 | 9/2015 | Huh et al. |
| 9,366,099 B2 | 6/2016 | Ly |
| 10,273,399 B2 | 4/2019 | Cox |
| 10,308,865 B2 | 6/2019 | Cox |
| 10,308,895 B2 | 6/2019 | Vidal et al. |
| 10,487,259 B2 | 11/2019 | Cox |
| 2003/0220204 A1 | 11/2003 | Baran et al. |
| 2004/0108110 A1 | 6/2004 | Zupanick et al. |
| 2005/0252286 A1 | 11/2005 | Ibrahim et al. |
| 2006/0105052 A1 | 5/2006 | Acar et al. |
| 2006/0293430 A1 | 12/2006 | Wang et al. |
| 2007/0114030 A1 | 5/2007 | Todd et al. |
| 2008/0110253 A1 | 5/2008 | Stephenson et al. |
| 2008/0111064 A1 | 5/2008 | Andrews et al. |
| 2009/0087911 A1 | 4/2009 | Rogerio |
| 2009/0087912 A1 | 4/2009 | Ramos et al. |
| 2009/0248309 A1 | 10/2009 | Nelville et al. |
| 2009/0277625 A1 | 11/2009 | Bai et al. |
| 2010/0049625 A1 | 2/2010 | Biebesheimer et al. |
| 2010/0092865 A1 | 4/2010 | Kanno et al. |
| 2010/0224823 A1 | 9/2010 | Yin et al. |
| 2010/0307745 A1 | 12/2010 | Lafitte et al. |
| 2011/0012331 A1 | 1/2011 | Kim |
| 2011/0030949 A1 | 2/2011 | Weaver et al. |
| 2011/0207231 A1 | 8/2011 | Natan et al. |
| 2011/0239754 A1 | 10/2011 | Dyer et al. |
| 2011/0257887 A1 | 10/2011 | Cooper et al. |
| 2011/0260051 A1 | 10/2011 | Preudhomme et al. |
| 2011/0275061 A1 | 11/2011 | Weidemaier et al. |
| 2012/0062886 A1 | 3/2012 | Piotti et al. |
| 2012/0115128 A1 | 5/2012 | Miller |
| 2012/0135080 A1 | 5/2012 | Bromberg et al. |
| 2012/0193578 A1 | 8/2012 | Pan et al. |
| 2012/0257199 A1 | 10/2012 | Liu et al. |
| 2012/0261617 A1 | 10/2012 | Pan et al. |
| 2012/0325465 A1 | 12/2012 | Hammer et al. |
| 2013/0040292 A1 | 2/2013 | Lopez et al. |
| 2013/0078469 A1 | 3/2013 | Winter et al. |
| 2013/0084643 A1 | 4/2013 | Commarieu et al. |
| 2013/0087329 A1 | 4/2013 | Hewitt et al. |
| 2013/0109261 A1 | 5/2013 | Koene |
| 2013/0244914 A1 | 9/2013 | Wu et al. |
| 2013/0259808 A1 | 10/2013 | Chen et al. |
| 2013/0296453 A1 | 11/2013 | Giesenberg et al. |
| 2013/0312970 A1 | 11/2013 | Lafitte et al. |
| 2013/0341030 A1 | 12/2013 | Brannon et al. |
| 2014/0060832 A1 | 3/2014 | Mahoney et al. |
| 2014/0077121 A1 | 3/2014 | Sun et al. |
| 2014/0120627 A1 | 5/2014 | Rubino et al. |
| 2014/0186939 A1 | 7/2014 | Peterman et al. |
| 2014/0190700 A1 | 7/2014 | Tang et al. |
| 2014/0231077 A1 | 8/2014 | Rivero et al. |
| 2014/0260694 A1 | 9/2014 | Szlendak |
| 2014/0323363 A1 | 10/2014 | Perriat |
| 2014/0360973 A1 | 12/2014 | Yin et al. |
| 2015/0013983 A1 | 1/2015 | Alwattari |
| 2015/0038347 A1 | 2/2015 | Johnson et al. |
| 2015/0050741 A1 | 2/2015 | Tour et al. |
| 2015/0079270 A1 | 3/2015 | Wang et al. |
| 2015/0118501 A1 | 4/2015 | Lu |
| 2015/0132543 A1 | 5/2015 | Nouzille et al. |
| 2015/0159079 A1 | 6/2015 | Huh et al. |
| 2015/0232747 A1 | 8/2015 | Kanj et al. |
| 2015/0268370 A1 | 9/2015 | Johnston et al. |
| 2015/0368547 A1 | 12/2015 | Lesko et al. |
| 2015/0376493 A1 | 12/2015 | Huh et al. |
| 2016/0003040 A1 | 1/2016 | Jessheim et al. |
| 2016/0040514 A1 | 2/2016 | Rahmani et al. |
| 2016/0083641 A1 | 3/2016 | Gamage |
| 2016/0097750 A1 | 4/2016 | Van Herzen et al. |
| 2016/0186044 A1 | 6/2016 | Rothrock et al. |
| 2016/0215030 A1 | 7/2016 | Bressner |
| 2016/0264846 A1 | 9/2016 | Bennetzen et al. |
| 2016/0304934 A1 | 10/2016 | Matsuno |
| 2017/0022804 A1 | 1/2017 | Gupta et al. |
| 2017/0059668 A1 | 3/2017 | Chang et al. |
| 2017/0199124 A1 | 7/2017 | Bolduc et al. |
| 2017/0350236 A1 | 12/2017 | Shen et al. |
| 2018/0171782 A1 | 6/2018 | Cox et al. |
| 2018/0265635 A1 | 9/2018 | Khamatnurova et al. |
| 2018/0275114 A1 | 9/2018 | Kosynkin et al. |
| 2019/0118265 A1 | 4/2019 | Nie et al. |
| 2019/0218907 A1 | 7/2019 | Ow et al. |
| 2019/0226326 A1 | 7/2019 | Ow et al. |
| 2019/0368336 A1 | 12/2019 | Hammond et al. |
| 2019/0382648 A1 | 12/2019 | Murugesan et al. |
| 2021/0025858 A1 | 1/2021 | Ow et al. |
| 2022/0305472 A1 | 9/2022 | Baker et al. |
| 2023/0417712 A1 | 12/2023 | Wang et al. |

FOREIGN PATENT DOCUMENTS

| | | |
|---|---|---|
| EP | 2040075 | 3/2009 |
| EP | 2480625 | 4/2013 |
| EP | 2480626 | 4/2013 |
| GB | 2489714 | 10/2012 |
| JP | 2005524849 | 8/2005 |
| JP | 2007514169 | 5/2007 |
| JP | 2008505259 | 2/2008 |
| JP | 2008524602 | 7/2008 |
| JP | 2009535060 | 10/2009 |
| JP | 2009540326 | 11/2009 |
| JP | 2015523073 | 8/2015 |
| WO | WO 2010138914 | 12/2010 |
| WO | WO 2011035292 | 3/2011 |
| WO | WO 2011035294 | 3/2011 |
| WO | WO 2011063023 | 5/2011 |
| WO | WO 2012154332 | 11/2012 |
| WO | WO 2012158478 | 11/2012 |
| WO | WO 2013142869 | 9/2013 |
| WO | WO 2014014919 | 1/2014 |
| WO | WO 2014066793 | 5/2014 |
| WO | WO 2014207075 | 12/2014 |
| WO | WO 2015044446 | 4/2015 |
| WO | WO 2015058206 | 4/2015 |
| WO | WO 2015097116 | 7/2015 |
| WO | WO 2015200060 | 12/2015 |
| WO | WO 2016015027 | 1/2016 |
| WO | WO 2016087397 | 6/2016 |
| WO | WO 2017011328 | 1/2017 |
| WO | WO 2017136641 | 8/2017 |
| WO | WO 2017164822 | 9/2017 |
| WO | WO 2018085504 | 5/2018 |
| WO | WO 2018175763 | 9/2018 |

OTHER PUBLICATIONS

Lachowicz, D. et al. "Biocompatible and fluorescent superparamagnetic iron oxide nanoparticles with superior magnetic properties coated with charged polysaccharide derivatives," Colloids and Surfaces B: Biointerfaces 150 (2017) 402-407, including graphical abstract (Year: 2017).*

Arora, V. et al. "Hydrophobically modified sodium alginate conjugated plasmonic magnetic nanocomposites for drug delivery & magnetic resonance imaging," Materials Today Communications 25 (2020) 101470, 11 pages and graphical abstract; Jul. 17, 2020 (Year: 2020).*

Pandey, S. et al. "On the Weak Intrinsic Luminescence from Paclitaxel Dissolved in Nonelectrolyte Solvents," Applied Spectroscopy, 53(8) 1999, pp. 991-999. (Year: 1999).*

Rippe, M. et al. "Synthesis and magnetic manipulation of hybrid nanobeads based on Fe3O4 nanoclusters and hyaluronic acid grafted with an ethylene glycol-based copolymer," Applied Surface Science 510 (2020) 145354, 10 pages; Jan. 12, 2020 (Year: 2020).*

(56) References Cited

OTHER PUBLICATIONS

Iordache, M.L. et al. "Magnetic chitosan grafted (alkyl acrylate) composite particles: Synthesis, characterization and evaluation as adsorbents," Arabian Journal of Chemistry (2018) 11, 1032-1043 (Year: 2018).*
U.S. Appl. No. 17/454,176, filed Nov. 9, 2021, Wang et al.
U.S. Appl. No. 17/454,181, filed Nov. 9, 2021, Wang et al.
U.S. Appl. No. 17/522,437, filed Nov. 9, 2021, Wang et al.
Agenet et al., "SPE 157019: Fluorescent Nanobeads: a First Step Toward Intelligent Water Tracers" Society of Petroleum Engineers, SPE International Oilfield Nanotechnology conference, Jun. 12-14, 2012, 13 pages.
Anisimov, "SPE 118862: The Use of Tracers for Reservoir Characterization" Society of petroleum Engineers (SPE), presented at SPE Middle East Oil and Gas Show and Conference, Mar. 15-18, 2009, 8 pages.
Armelao et al., "Design of luminescent lanthanide complexes: From molecules to highly efficient photo-emitting materials" Coordination Chemistry Reviews, vol. 254, 5-6, Mar. 2010, 19 pages.
Aslan et al., "Fluorescent Core-Shell AG@$SiO_2$ Nanocomposites for Metal-Enhanced Fluorescence and Single Nanoparticle Sensing Platforms" Jan. 19, 2007, 2 pages.
Badgett et al., "Totalsynthese eines Neobetanidin-Derivates und des Neobetenamins" Helvetica Chimica Acta, 1970, 53(2): 433-448, 16 pages (English Abstract).
Bagaria et al., "Iron Oxide Nanoparticles Grafted with Sulfonated Copolymers are Stable in Concentrated Brine at Elevated Temperatures and Weakly Adsorb on Silica" ACS Applied Materials & Interfaces, vol. 5, No. 8, Mar. 25, 2013, 3329-3339, 11 pages.
Bala et al., "Interaction of Different Metal Ions with Carboxylic Acid Group: A Quantitative Study" The Journal of Physical Chemistry A, vol. 111, No. 28, Jun. 2007, 6183-6190, 8 pages.
Bao et al., "Luminescence properties of the co-luminescence groups of Sm-La-pyridyl carboxylic acids" Journal of Rare Earths, 30(4), Apr. 2012, 320-324, 5 pages.
Blachier et al., "Adsorption of polyamine on clay minerals" Journal of Colloid and Interface Science, 336, Aug. 2009, 599-606, 8 pages.
Borrini et al., "Water Soluble PDCA Derivatives for Selective Ln(III)/An(III) and Am(III)/Cm(III) Separation" Solvent Extraction and Ion Exchange, 33(3), Oct. 2014, 224-235, 30 pages.
Brichart et al., "The Use of Fluorescent Tracers for Inhibitor Concentration Monitoring Useful for Scale Inhibitor" International Petroleum Technology Conference, IPTC-17933-MS, presented at the International Petroleum Technology Conference held in Kuala Lumpur, Malaysia, Dec. 10-12, 2014, 8 pages.
Bunzil et al., "Taking advantage of luminescent lanthanide ions" Chemical Society Reviews, Dec. 2005, 29 pages.
Chang et al., "Magnetic SERS Composite Nanoparticles for Microfluidic Detection" 251st ACE National Meeting, Mar. 13-17, 2016, 1 page.
Chen et al., "Aggregation Kinetics of Alginate-Coated Hematite Nanoparticles in Monovalent and Divalent Electrolytes" Environmental Science & Technology, vol. 40, No. 5, Mar. 2006, 1516-1523, 9 pages.
Chen et al., "Analysis of the solution conformations of T4 lysozyme by paramagnetic NMR spectroscopy" Physical Chemistry Chemical Physics, 2016, 18(8), 5850-5859, 10 pages.
Chen et al., "Impact of Irreversible Retention on Tracer Deployments; Constraining Novel Material Deployments" SPE 188890-MS, in SPE Abu Dhabi International Petroleum Exhibition and Conference, Society of Petroleum Engineers, Nov. 2017, 8 pages.
Chen et al., "Improved Reservoir History Matching and Prudction Optimization with Tracer Data" SPE 191523-MS, in SPE Annual Technical Conference and Exhibition, Society of Petroleum Engineers, Sep. 2018, 15 pages.
Chen et al., "Upconversion Nanoparticles: Design, Nanochemistry, and Applications in Theranostics" Chem. Rev, 114(10), Mar. 2014, 5161-5214, 54 pages.
Chen et al., "FITC functionalized magnetic core-shell $Fe_3O_4$/Ag hybrid nanoparticle for selective determination of molecular biothiols" Elsevier Ltd., Dec. 2013, 7 pages.
Chen et al.; "Hydration Repulsion between Carbohydrate Surfaces Mediated by Temperature and Specific Ions" Scientific Reports, vol. 6, Jun. 23, 2016, 10 pages.
Cheraghian, "Application of nano-particles of clay to improve drilling fluid" Int. J. Nanosci. Nanotechnol., 13, Jun. 2017, 177-186, 10 pages.
Chuang et al., "Ultra-sensitive in-situ detection of novel near-infrared persistent luminescent tracer nanoagents in crude oil-water mixtures" a natureresearch journal, Scientific Reports, Jun. 15, 2016, 5 pages.
Coates et al., "Enhancement of luminescence of europium(m) ions in water by use of synergistic chelation. Part 1.1 : 1 and 2 : 1 complexes" J. Chem. Soc, Perkin Trans., Jan. 1996, 1275-1282, 8 pages.
Cole et al.; "Polyethylene Glycol Modified, Cross-Linked Starch-Coated Iron Oxide Nanoparticles for Enhanced Magnetic tumor Targeting" Biomaterials, vol. 32, No. 8, Mar. 1, 2011, 2183-2193, 11 pages.
Cox et al., "Pyrolyzable Nanoparticle Tracers for Environmental Interrogation and Monitoring" ACS Appl. Mater. Interfaces, 2017, 9(15), 13111-13120, 10 pages.
Cubillos et al., "SPE 174394-MS: The Value of Inter-well and Single Well Tracer Technology for De-Risking and Optimizing a CEOR Process—Caracara Field Case" Society of Petroleum Engineers (SPE), presented at EUROPEC 2015, Jun. 1-4, 2015, 19 pages.
Das et al., "Molecular Fluorescence, Phosphorescence, and Chemiluminescence Spectrometry" Analytical Chemistry, Nov. 3, 2011, 29 pages.
Deans, "SPE 7076: Using Chemical Tracers To Measure Fractional Flow And Saturation In-Situ" Society of Petroleum Engineers (SPE), presented at SPE Symposium on improved Methods of Oil Recovery, Apr. 16-17, 1978, 10 pages.
Deschamps et al., "Drilling to the Extreme: the Micro-Coring Bit Concept" IADC/SPE 115187, presented at the IADC/SPE Asai Pacific Drilling Technology Conference and Exhibition, Aug. 25-27, 2008, 12 pages.
Desmette et al., "Drilling Hard and Abrasive Rock Efficiently, or Generating Quality Cuttings? You No Longer Have to Choose . . . " SPE 116554, Society of Petroleum Engineers, 2008 SPE Annual Technical Conference and Exhibition, Sep. 21-24, 2008, 19 pages.
Du et al., "SPE 93140: Interwell Tracer Tests: Lessons Learnted from past Field Studies" Society of Petroleum Engineers (SPE), presented at SPE Asia Pacific Oil and Gas Conference and Exhibition, Apr. 5-7, 2005, 9 pages.
Dugstad, "Chapter 6: Well-to-well tracer tests" in Petroleum Engineering Handbook, 2007, 651-683, 31 pages.
Dung et al., "Structural and magnetic properties of starch coated magnetite nanoparticles" Journal of Experimental Nanoscience, 4, Sep. 2009, 259-267, 9 pages.
Edwards et al., "Extending the distance range accessed with continuous wave EPR with Gd3+ spin probes at high magnetic fields" Physical Chemistry Chemical Physics, 15(27), 2013, 11313-11326, 14 pages.
El-Aneed et al., "Mass Spectrometry, Review of the Basics: Electrospray, MALDI, and Commonly Used Mass Analyzers" Applied Spectroscopy Reviews, Mar. 16, 2009, 22 pages.
Fichtel et al., "A highly sensitive HPLC method for determination of nanomolar concentrations of dipicolinic acid, a characteristic constituent of bacterial endospores" Journal of Microbiological Methods, 2007, 70, 319-327, 9 pages.
Freeze and Cherry, "Chapter 9: Groundwater Contamination" in Groundwater, Englewood Cliffs, NJ: Prentice-Hall, Inc., 1979, 80 pages.
Galdiga and Greibrokk, "Ultra-trace determination of flurinated aromatic carboxylic acids in aqueous reservoir fluids using solid-phase extraction in combination with gas chromatography-mass spectrometry" Journal of Chromatography, vol. 793, Issue 2, Apr. 1997, 297-306, 10 pages.
Gao et al., "A Surface Functional Monomer-Directing Strategy for Highly Dense Imprinting of TNT at Surface of Silica Nanoparticles" Journal of American Chemical Society, vol. 129, No. 25, Jun. 2007, 7859-7866, 8 pages.

(56) References Cited

OTHER PUBLICATIONS

Gardiner et al., "Practical Raman Spectroscopy" Springer-Verlag, 1989, 9 pages.
Ge et al., "Fluorescence modified chitosan coated magnetic nanoparticles for high-efficienct cellular imaging" Nanoscale Res. Lett, 4, Jan. 2009, 287-295, 9 pages.
George et al., "Modified Dipicolinic Acid Ligands for Sensitation and Europium (III) Luminescence" Inorganic Chemistry, vol. 45, No. 4, Feb. 1, 2006, 6 pages.
Georgi, et al., "Advances in Cuttings Collection and Analysis" SPWLA 34th Annual Logging Symposium, Jun. 13-16, 1993, 20 pages.
Gordon-Grossman et al., "W-Band pulse EPR distance measurements in peptides using Gd3+-dipicolinic acid derivatives as spin labels" Physical Chemistry Chemical Physics, 13(22), 2011, 10771-10780, 10 pages.
Grutzke et al., "Heptacoordinate Heteroleptic Salan (ONNO) and Thiosalan (OSSO) Titanium(IV) Complexes: Investigation of Stability and Cytotoxicity" Inorganic Chemistry 54(14), Jul. 2015, 6697-6706, 10 pages.
Hagoot, "The response of interwell tracer tests in watered-out reservoirs" SPE 11131-MS, in SPE Annual Technical Conference and Exhibition, Society of Petroleum Engineers, Jan. 1982, 21 pages.
Han et al., "Application of Silver-Coated Magnetic Microspheres to a SERS-Based Optofluidic Sensor" The Journal of Physical Chemistry (JPCC), Mar. 7, 2011, 7 pages.
Hardy et al., "A novel fluorescent tracer for real-time tracing of clay transport over soil surfaces" Catena, 141, Jun. 2016, 39-45, 7 pages.
He et al., "Luminescent Europium Chelates Synthesis and Fluorescence Properties" Sensors and Materials (2007), 19(2), 123-132, 10 pages.
Hindle et al., "Dipicolinic acid (DPA) assay revisited and appraised for spore detection" Analyst, 1999, 124: 1599-1604, 6 pages.
Hu et al., "Smart Liquid SERS Substrates based on $Fe_3O_4$/Au Nanoparticles with Reversibility Tunable Enhancement Factor for Practical Quantitative Detection" a natureresearch journal, Scientific Reports, Nov. 27, 2014, 10 pages.
Huseby et al., "Assessing EOR potential from partitioning tracer data" SPE 172808-MS, in SPE Middle East Oil and Gas Show and Conference, Society of Petroleum Engineers, Mar. 2015, 15 pages.
Huseby et al., "SPE-169183-MS: High Quality Flow Information from Tracer Data" Society of Petroleum Engineers (SPE), presented at the SPE Bergen One Day Seminar, Apr. 2, 2014, 9 pages.
Hutchins et al., "SPE-21049: Aqueous Tracers for Oilfield Applications" Society of Petroleum Engineers (SPE), presented at SPE International Symposium on Oilfield Chemistry, Feb. 20-22, 1991, 9 pages.
Invitrogen, "Fluorophores and Their Amine-Reactive Derivatives" Molecular Probs Handbook, A Guide to Fluorescent Probes and Labeling Technologies, 11th Edition, 2010, 88 pages.
Jenkins et al., "Ultratrace Determination of Selected Lanthanides by Luminescence Enhancement" Analytical Chemistry, vol. 68, No. 17, Jan. 1, 1996, 7 pages.
Jun et al., "Multifunctional Silver-Embedded Magnetic Nanoparticles as SERS Nanoprobes and Their Applications" Wiley-VCH Verlag GmbH& Co. KGaA, Weinheim, Jan. 4, 2010, 7 pages.
Kaushik et al., "Gd(III) and Mn(II) complexes for dynamic nuclear polarization: small molecular chelate polarizing agents and applications with site-directed spin labeling of proteins" Physical Chemistry Chemical Physics, 18(39), 2016, 27205-27218, 36 pages.
Khan et al., "Optimizing waterflood management in a giant UAE carbonate oil field using simulation-based streamlines" SPE 171777-MS, in Abu Dhabi International Petroleum Exhibition and Conference, Society of Petroleum Engineers, Nov. 10-13, 2014, 9 pages.
Kneipp et al., "Single Molecule Detection Using Surface-Enhanced Raman Scattering (SERS)" Physical Review Letters, American Physical Society vol. 78, No. 9, Mar. 3, 1997, 4 pages.
Kornberger and Thiele, "Experiences with an Efficient Rate-Management Approach for the 8th Tortonian Reservoir in the Vienna Basin" SPE 166393-PA, SPE Reservoir Evaluation and Engineering, vol. 17, No. 2, May 2014, 12 pages.
Kosynkin and Alaskar, "Oil Industry First Interwell Trial of Reservoir Nanoagent Tracers" SPE 181551-MS, in SPE Annual Technical Conference and Exhibition, Society of Petroleum Engineers, Sep. 2016, 15 pages.
Kramer, "Water-Soluble Dendritic Architectures with Carbohydrate Shells for the Templation and Stabilization of Catalytically Active Metal Nanoparticles" published by ACS, Macromolecules, vol. 38, No. 20, Aug. 27, 2005, 8308-8315, 8 pages.
Labbe et al., "Development of metal-chelating inhibitors for the Class II fructose 1,6-bisphosphate (FBP) aldolase" Journal of Inorganic Biochemistry, 112, Jul. 2012, 49-58, 10 pages.
Lachowicz et al., "Biocompatible and fluorescent superparamagnetic iron oxide nanoparticles with superior magnetic properties coates with charged polysaccharide derivatives" Colloids and Surfaces B: Biointerfaces, 2017, 150, 402-407, 18 pages.
Larsen et al., "Efficient Synthesis of 4,7-Diamino Substituted 1,10-Phenanthroline-2,9-dicarboxamides" Organic Letters, vol. 13, No. 13, Jul. 2011, 3546-3548, 3 pages.
Li et al., "Long persistent phosphors—from fundamentals to applications" Chem. Soc. Rev., 45(8), Apr. 2016, 2090-2136, 48 pages.
Li et al., "Magic Angle Spinning NMR Structure Determination of Proteins from Pseudocontact Shifts" Journal of the American Chemical Society, 135(22), May 2013, 8294-8303, 10 pages.
Li et al., "Superparamagnetic Iron Oxide Nanoparticles as MRI contrast agents for Non-invasive Stem Cell Labeling and Tracking" Theranostics, Jul. 2013, 3(8):595-615, 21 pages.
Li et al., "Thiol-ene reaction: a versatile tool in site-specific labelling of proteins with chemically inert tags for paramagnetic NMR" Chemical Communications, Cambridge, United Kingdom, 48(21), 2704-2706, 2012, 18 pages, supporting information only.
Liu et al., "Photostimulated near-infrared persistent luminescence as a new optical read-out from Cr3+-doped $LiGa_5O_8$" Scientific Reports 3, Article 1554, Mar. 2013, 9 pages.
Lomstein and Jorgensen, "Pre-column liquid chromatographic determination of dipicolinic acid from bacterial endospores" Limnology and Oceanography: Methods, Apr. 2012, 10:4, 227-233, 14 pages.
Mahdavi et al., "Preparation, Characterization, and Application of Polyacrylamide-Polystyrene/Bentonite Nanocomposite as an Effective Immobilizing Adsorbent for Remediation of Soil" Chemistry Select, 5, Apr. 2020, 4538-4547, 12 pages.
Mahmoudi et al., "Superparamagnetic iron oxide nanoparticles development surface modification and applications in chemotherapy" Advanced Drug Delivery Reviews, Jan. 2011, 63, 24-46, 23 pages.
Manna et al., "Complexation behavior of trivalent actinides and lanthanides with 1,10-phenanthroline-2,9-dicarboxylic acid based ligands: insight from density functional theory" Physical Chemistry Chemical Physics, vol. 14, No. 31, Jan. 2012, 11060-11069, 10 pages.
Marais, A., et al. "Time-Resolved Fluorescence for Real-Time Monitoring of Both Scale and Corrosion Inhibitors: A Game-Changing Technique" SPE International Oilfield Scale Conference and Exhibition. OnePetro, May 2016, 11 pages.
Marchetti et al., "Fluorous affinity chromatography for enrichment and determination of perfluoroalkyl substances" Annual Review of Analytical Chemistry vol. 84, Jul. 19, 2012, 8 pages.
Martinez et al., "Polysaccharide-based Nanoparticles for Controlled Release Formulations" The Delivery of Nanoparticles, Published May 2012, 185-222, 40 pages.
Martini et al., "How to Monitor Scale Inhibitor Squeeze using Simple TRF Tracers" Society of Petroleum Engineers, presented at the SPE International Symposium on Oilfield Chemistry held in the Woodlands, Texas, Apr. 13-15, 2015, 8 pages.
Melton et al, "Complexes of Greatly Enhanced Thermodynamic Stability and Metal Ion Size-Based Selectivity, Formed by the Highly Preorganized Non-Macrocyclic Ligand 1,10-Phenanthroline-2,9-dicarboxylic Acid: A Thermodynamic and Crystallographic Study" Inorganic Chemistry vol. 45 No. 23, Jun. 2006, 9 pages.
Moyner et al., "The Application of Flow Diagnostics for Reservoir Management" Society of Petroleum Engineers (SPE), Apr. 2015, 18 pages.

(56) References Cited

OTHER PUBLICATIONS

Muller and Seubert, "Ultra trace determination of fluorobenzoic acids in tap and reservoir water using solid-phase extraction and gas chromatography-mass spectrometry" Journal of Chromatography A, 1260, Oct. 2012, 7 pages.

Nie et al., "Probing Single Molecules and Single Nanoparticles by Surface-Enhanced Raman Scattering" Science, vol. 275, No. 5303, Feb. 1997, 1102-1106, 6 pages.

Ogden et al., "Complexation of Am(III) and Nd(in) by 1,10-Phenanthroli ne-2,9-Di carboxylic Acid" Journal of Solution Chemistry, vol. 42, No. 1, pp. 211-225, 2013, 15 pages.

Ouali et al., "Analysis of Paramagnetic NMR Spectra of Triple-Helical Lanthanide Complexes with 2,6-Dipicolinic Acid Revisited: A New Assignment of Structural Changes and Crystal-Field Effects 25 Years Later" Inorganic Chemistry, 41(6), Feb. 2002, 1436-1445, 10 pages.

Pallenberg et al. "Synthesis and Characterization of Some Copper(I) Phenanthroline Complexes" Inorg. Chem. 1995, 34, 2833-2840, 8 pages.

Park et al., "Application of montmorillonite in bentonite as a pharmaceutical excipient in drug delivery systems" Journal of Pharmaceutical Investigation, 46, May 2016, 363-375, 13 pages.

Parker and Williams, "Getting excited about lanthanide complexation chemistry" Journal of the Chemical Society, Dalton Transactions, vol. 18, 1996, 16 pages.

Parker et al., "Being excited by lanthanide coordination complexes: aqua species, chirality, excited- state chemistry, and exchange dynamics" Chemical Reviews, vol. 102, Issue 6, May 2002, 34 pages.

Petoud et al., "Brilliant SM, Eu, Tb, and Dy Chiral Lanthanide Complexes with Strong Circularly Polarized Luminescence" Journal fo the American Chemical Society (JACS), Dec. 15, 2006, 7 pages.

Potapov et al., "Nanometer-Scale Distance Measurements in Proteins Using Gd3+ Spin Labeling" Journal of the American Chemical Society, 132(26), Jun. 2010, 9040-9048, 9 pages.

Qianming et al., "Bspda Synthesis and its Europium (III) Complexes' Fluorescence" Chemical Industry Times, Jul. 2005, 19(7): 38-41, 4 pages (English Abstract).

Rashdan et al., "Effect of the preparation route, PEG and annealing on the phase stability of Fe304 nanoparticles and their magnetic properties" Journal of Experimental Nanoscience, vol. 8, No. 2, 2013, 210-222, 13 pages.

Rovani, "Enhanced Oil Recovery: Aqueous Flow Tracer Measurement" WRI-09-R002, OSTI.Gov, Technical Report, U.S. Department of Energy, Feb. 2009, 1-18, 25 pages.

Rowan et al., "Dynamic Covalent Chemistry" Angewante Chemie International Edition, Mar. 15, 2002, 55 pages.

Sabbatini et al., "Luminescent lanthanide complexes as photochemical supramolecular devices" Coordination Chemistry Reviews, vol. 123, issue 1-2, Feb. 1993, 28 pages.

Saeki et al., "Upper and lower critical solution temperatures in poly (ethylene glycol) solutions" POLYMER, vol. 17, No. 8, Aug. 1976, 685-689, 5 pages.

Sammes and Yshioglu, "Modern bioassays using metal chelates as luminescent probes" Natural Product Reports, vol. 31, No. 1, 1996, 28 pages.

Sanni et al., "A field case study of inter-well chemical tracer test" in SPE International Symposium on Oilfield Chemistry, Society of Petroleum Engineers, Apr. 2015, 17 pages.

Sanni et al., "Pushing the envelope of residual oil measurement: A field case study of a new class of inter-well chemical tracers" Journal of Petroleum Science and Engineering, vol. 163, 2018, 19 pages.

Santarelli et al., "Formation Evaluation From Logging on Cuttings" SPE Reservoir Evaluation and Engineering, presented at the 1996 SPE Permian Basin Oil and Gas Recovery Conference, Mar. 27-29, 1996, published Jun. 1998, 7 pages.

Schmidt et al., "Copper dipicolinates as peptidomimetic ligands for the Src SH2 domain" Bioorganic & Medicinal Chemistry Letters, 14(16), 4203-4206, Aug. 2004, 4 pages.

Schmidt et al., "Synthesis of Mono- and Dinuclear Vanadium Complexes and Their Reactivity toward Dehydroperoxidation of Alkyl Hydroperoxides" Inorganic Chemistry 56(3), 2017, 1319-1332, 14 pages.

Selvin et al., "Principles and biophysical applications of lanthanide-based probes" Annual Review of Biophysics and Biomolecular Structure, Jun. 2002, 28 pages.

Serres-Piole et al., "Direct sensitive simultaneous determination of fluorinated benzoic acids in oil reservoir waters by ultra high-performance liquid chromatography-tandem mass spectrometry" Journal of Chromatography A, 1218, Aug. 2011, 6 pages.

Serres-Piole et al., "Water tracers in oilfield applications: Guidelines" Elsevier Ltd., Journal of Science and Engineering, Nov. 2012, 18 pages.

ShamsiJazeyi et al., "Polymer-Coated Nanoparticles for Enhance Oil Recovery" Journal of Applied Polymer Science, vol. 131, No. 15, Aug. 5, 2014, 13 pages.

Shook et al., "SPE 124614: Determining Reservoir Properties and Flood Performance from Tracer Test Analysis" Society of petroleum Engineers (SPE), presented at SPE Annual Technical Conference and Exhibition, Oct. 4-7, 2009, 19 pages.

Solomon et al., "Synthesis and Study of Silver Nanoparticles" Journal of Chemical Education vol. 84, No. 2, 2007, 332-325, 4 pages.

Song et al., "SERS-Encoded Nanogapped Plasmonic Nanoparticles: Growth of Metallic Nanoshell by Templating Redox-Active Polymer Brushes" Journal of the American Chemical Society (JACS), Apr. 28, 2014, 4 pages.

Stiles et al., "Surface-Enhanced Raman Spectroscopy" Annual Review of Analytical Chemistry, vol. 1, No. 1, Jul. 2008, 601-626, 29 pages.

Stryer et al., "Diffusion-enhanced fluorescence energy transfer" Annual Review of Biophysics and bioengineering, vol. 11, Issue 1, 1982, 21 pages.

Su et al., "A Dipicolinic Acid Tag for Rigid Lanthanide Tagging of Proteins and Paramagnetic NMR Spectroscopy" Journal of the American Chemical Society, 130(32), Jul. 2008, 10486-10487, 2 pages.

Tang et al., "Synthesis and fluorescence properties of Tb(III) complexes with pyridine-2,6-dicarboxylic acid derivatives" Journal of Central South University of Technology (English Edition), 15(5), Oct. 2008, 599-605, 7 pages.

Tang et al., "Synthesis of Novel Derivatives of Pyridine-2,6-dicarboxylic Acid" Synthetic Communications: An International Journal for Rapid Communication of Synthetic Organic Chemistry, 36(14), Jun. 2006, 2027-2034, 9 pages.

Tang et al., "Synthesis of Eu(III) and Tb(III) Complexes with Novel Pyridine-2,6-Dicarboxylic Acid Derivatives and Their Fluorescence Properties" Front. Chem. China, 2006, 4:, 408-413, 6 pages.

Thomas et al., "Deployment and Detection of a Novel Barcoded Advanced Tracers System for the Optimization of Improved Waterflood Recovery in Hydrocarbon Reservoirs" SPE-194872-MS, SPE Middle East Oil and Gas Show and Conference. Society of Petroleum Engineers, 2019, 10 pages.

Tian et al., "Off-Resonant Gold Superstructures as Ultrabright Minimally Invasive Surface-Enhanced Raman Scattering (SERS) Probes" American Chemical Society, Jul. 2015, 7 pages.

Toulhoat, "Experimentation and Modelling of U, Th and Lanthanides Transport in Fissured Rocks: Influence of Complexation" MRS Proceedings, vol. 50, Jan. 1, 1985, 8 pages.

Wahajuddin et al., "Superparamagnetic iron oxide nanoparticles: Magnetic nanoplatforms as drug carriers" International Journal of Nanomedicine, 7, Jul. 2012, 3445-3471, 27 pages.

Wang et al., "The Design and Implementation of a Full Field Inter-Well Tracer Program on a Giant UAE Carbonate Oil Field" in Abu Dhabi International Petroleum Exhibition and Conference, Society of Petroleum Engineers, SPE-177527-MS, Nov. 2015, 8 pages.

(56) References Cited

OTHER PUBLICATIONS

Wu et al., "A reusable biosensor chip for SERS-fluorescence dual mode immunoassay" Proc. SPIE 9543, Third International Symposium on Laser Interaction with Matter, 954317, May 4, 2015, 6 pages.

Wu et al., "A SERS-Assisted 3D Barcode Chip for High-Throughput Biosensing" Small Journal vol. 11, No. 23, Jun. 11, 2015, 9 pages.

Xu et al., "Superparamagnetic Photonic Crystals" Adv. Mater., Nov. 2001, 13, 1681-1683, 4 pages.

Xu et al., "Synthesis and Utilization of Monodisperse Superparamagnetic Colloidal Particles for Magnetically Controllable Photonic Crystals" Chem. Mater., 14(3), 2002, 1249-1256, 8 pages.

Xu et al.., "Measurement of two-photon excitation cross sections of molecular fluorophores with data from 690 to 1050 nm" Journal of the Optical Society of America B, Mar. 1996, 11 pages.

Yang et al., "The Co-Luminescence Groups of Sm-La-pyridyl Carboxylic Acids and the Binding Characteristics between the Selected Doped Complex and Bovine Serum Albumin" Bulletin of the Korean Chemical Society 33(4), Apr. 20, 2012, 1303-1309, 7 pages.

Yang et al., "Paramagnetic labeling of proteins and pseudocontact shift in structural biology" Chinese Journal of Magnetic Resonance, 2014, 31(2):155-171, 12 pages (English Abstract).

Yu et al., "Adsorption of proteins and nucleic acids on clay minerals and their interactions: A review" Applied Clay Science, 80-81, Aug. 2013, 443-452, 10 pages.

Zamberi et al., "SPE 166005: Improved Reservoir Surveillance Through Injected Tracers In A Saudi Arabian Field: Case Study" Society of Petroleum Engineers (SPE), presented at SPE Reservoir Characterization and Simulation Conference and Exhibition, Sep. 2013, 15 pages.

Zemel, "Chapter 3: Interwell Water Tracers" Tracers in the Oil Field, vol. 43, 1st Edition, Elsevier Science, Jan. 13, 1995, 47 pages.

Zhang et al., "Water adsorption on kaolinite and illite after polyamine adsorption" Journal of Petroleum Science and Engineering, 142, Jun. 2016, 13-20, 8 pages.

Zhao et al., "Chromatographic Separation of Highly Soluble Diamond Nanoparticles Prepared by Polyglycerol Grafting" Angewandte Chemie International Edition, vol. 50, No. 6, Feb. 7, 2011, 1388-1392, 5 pages.

Zhou et al., "Upconversion luminescent materials: advances and applications" Chem Rev., Jan. 14, 2015, 71 pages.

\* cited by examiner

200

200

200

300

MULTIFUNCTIONAL POLYSACCHARIDE-BASED MUD LOGGING BARCODE TRACERS

TECHNICAL FIELD

This document relates to methods and compositions used in tagging and tracing subterranean rock cuttings produced during drilling.

BACKGROUND

Subterranean rock cuttings that are produced during drilling operations can provide critical information, for example, the lithology and mineral composition of the subterranean formation. However, cuttings produced at the drill head travel to the surface via the annulus, and it is difficult to accurately determine or even estimate lag time during this upward trip. This makes analyzing the depth at which these cuttings originated difficult.

Mud tracers can be used to determine mud cycle time, for example, the circulation time, however, the estimating the origin depth of rock cuttings based on circulation time is inaccurate, especially if the wellbore includes long horizontal sections or the return trip time is lengthy. For example, when the return trip is longer than half an hour, it is common to have depth uncertainties of more than 6 meters (20 feet). This, in turn, compounds errors in characterizing the formation according to the depth of the cuttings. More efficient mud tracer materials and rapid detection techniques for these tracers are highly desirable.

SUMMARY

This disclosure describes compositions and methods that can be used to determine the origin depth of a wellbore rock cutting.

In some implementations, a nanoparticle tag includes a natural polysaccharide, a fluorescent dye, and superparamagnetic nanoparticles.

In some implementations, a method of making a nanoparticle tag includes functionalizing a natural polysaccharide with a fluorescent dye, and incorporating superparamagnetic nanoparticles into the nanoparticle tag.

In some implementations, a method of determining the origin location of a subterranean rock sample includes mixing a nanoparticle tag into a fluid. The nanoparticle tag includes a natural polysaccharide core that includes a fluorescent dye and superparamagnetic nanoparticles. The method includes flowing the fluid through a work string into a subterranean formation, recovering subterranean rock samples from the subterranean formation, separating tagged rock samples from untagged rock samples using a magnet, and determining the origin location of the subterranean rock sample by analyzing the fluorescent signal of the nanoparticle tag.

In some implementations, a method of tagging and tracing cut subterranean rock includes using a barcode mud tracer in a drilling fluid to tag a cut subterranean rock produced during drilling. The barcode mud tracer includes a nanoparticle tag. The nanoparticle tag includes a natural polysaccharide, a fluorescent dye, superparamagnetic nanoparticles, and a polymer coating. The method includes identifying the barcode mud tracer using two or more orthogonal analytical techniques.

The details of one or more implementations of the disclosure are set forth in the accompanying drawings and the description that follows. Other features, objects, and advantages of the disclosure will be apparent from the description and drawings, and from the claims.

DESCRIPTION OF DRAWINGS

Like reference symbols in the various drawings indicate like elements.

DETAILED DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Provided in this disclosure, in part, are tags, methods, and systems for tagging rock cuttings produced during a drilling operation. These tags, methods, and systems can be used to determine the origin location of a rock cutting or subterranean rock sample. The tags can absorb to, permanently, or semi-permanently decorate rock cuttings or subterranean rock samples. The tags can be identified by multiple orthogonal techniques, and therefore the various combinations of orthogonally detectable features create a library of uniquely identifiable tags.

Figure 1:
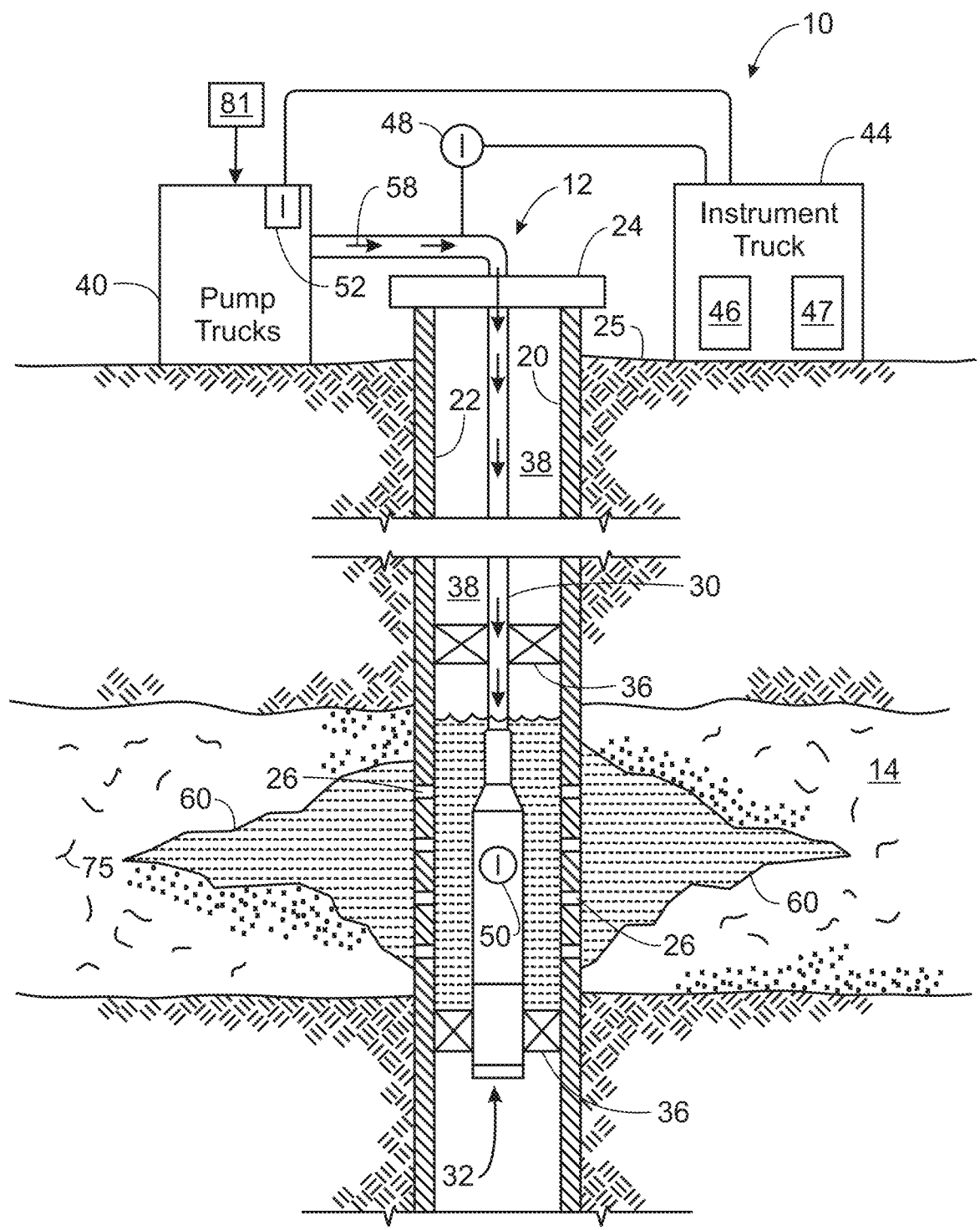
FIG. 1 shows a schematic of an example of a drilling operation.

FIG. 1 illustrates an example of a drilling operation 10 for a well 12. The well 12 can be in a wellbore 20 formed in a subterranean zone 14 of a geological formation in the Earth's crust. The subterranean zone 14 can include, for example, a formation, a portion of a formation, or multiple formations in a hydrocarbon-bearing reservoir from which recovery operations can be practiced to recover trapped hydrocarbons. Examples of unconventional reservoirs include tight-gas sands, gas and oil shales, coalbed methane, heavy oil and tar sands, gas-hydrate deposits, to name a few. In some implementations, the subterranean zone 14 includes an underground formation including natural fractures 60 in rock formations containing hydrocarbons (for example, oil, gas, or both). For example, the subterranean zone 14 can include a fractured shale. In some implementations, the well 12 can intersect other suitable types of formations, including reservoirs that are not naturally fractured in any significant amount.

The well 12 can include a casing 22 and well head 24. The wellbore 20 can be a vertical, horizontal, deviated, or multilateral bore. The casing 22 can be cemented or otherwise suitably secured in the wellbore 20. Perforations 26 can be formed in the casing 22 at the level of the subterranean zone 14 to allow oil, gas, and by-products to flow into the well 12 and be produced to the surface 25. Perforations 26 can be formed using shape charges, a perforating gun, or otherwise.

For a drilling treatment 10, a work string 30 can be disposed in the wellbore 20. The work string 30 can be coiled tubing, sectioned pipe, or other suitable tubing. A drilling tool or drill bit 32 can be coupled to an end of the work string 30. Packers 36 can seal an annulus 38 of the wellbore 20 uphole of and downhole of the subterranean zone 14. Packers 36 can be mechanical, fluid inflatable, or other suitable packers.

One or more pump trucks 40 can be coupled to the work string 30 at the surface 25. The pump trucks 40 pump drilling mud 58 down the work string 30 to lubricate and cool the drilling tool or drill bit 32, maintain hydrostatic pressure in the wellbore, and carry subterranean rock cuttings to the surface. The drilling mud 58 can include a fluid pad, proppants, flush fluid, or a combination of these components. The pump trucks 40 can include mobile vehicles, equipment such as skids, or other suitable structures.

One or more instrument trucks 44 can also be provided at the surface 25. The instrument truck 44 can include a drilling control system 46 and a drilling simulator 47. The drilling control system 46 monitors and controls the drilling treatment 10. The drilling control system 46 can control the pump trucks 40 and fluid valves to stop and start the drilling treatment 10. The drilling control system 46 communicates with surface and subsurface instruments to monitor and control the drilling treatment 10. In some implementations, the surface and subsurface instruments may comprise surface sensors 48, down-hole sensors 50, and pump controls 52.

Additives 81 can be mixed with drilling mud 58 and flowed through the reservoir. In some implementations, the additives are tags that can embed into, permanently, or semi-permanently decorate the surface of rock cuttings produced by the drill bit. When drilling mud is introduced into the subterranean formation via the drill bit, tags that are included in the mud will contact the subterranean formation for the first time at the drill head. If the depth or relative position of the drill head and the lag time of the mud in the drill string are known, rock cuttings that are tagged with a specific tag can be accurately assigned an origin depth or position. Accordingly, the origin location of the rock cutting can be accurately determined.

In some implementations, more than one tag can be used. The tags can be uniquely identifiable. Accordingly, rock cuttings that include or are decorated with a first tag can be assigned to a first depth or position, and rock cuttings that include or are decorated with a second tag can be assigned to a second depth or position.

The tags described herein are multi-modal tags, meaning that each tag includes a unique combination of features that can be orthogonally detected. Accordingly, the variations in the features of the tags can act as a uniquely identifiable "barcode." In addition, the combination of orthogonally detectable features expands the number of uniquely identifiable tags that can be produced and uniquely identified.

Further, the tags described herein can be rapidly detected with high sensitivity. In some implementations, the tags can be detected at the drilling site, making detection more rapid and allowing the drill operators to make drilling decisions based on real-time data.

Another advantage of the tags described herein is that they can be identified in two stages. In a first stage, tagged rock samples can be separated quickly from untagged rock samples in a first procedure. After the separation, the tagged materials can be subjected to additional analysis, either off-site or on-site. Accordingly, the multi-stage approach includes a first separation that acts as a screening process. The screening process concentrates the tagged rock samples. In addition, if the rock samples require subsequent off-site analysis, the screening process reduces the number of rock samples that need to be transported and subsequently analyzed. This approach saves time, labor, and laboratory costs. In addition, this multi-modal identification allows for rapid identification and real-time analysis that can aid in drilling operations.

Provided herein are tags for identifying the origin depth of a rock cutting produced during drilling. The tags are composite nanoparticles, with multi-functional aspects that can be detected through multiple types of analysis, including through orthogonal analytical techniques.

Figure 2A:
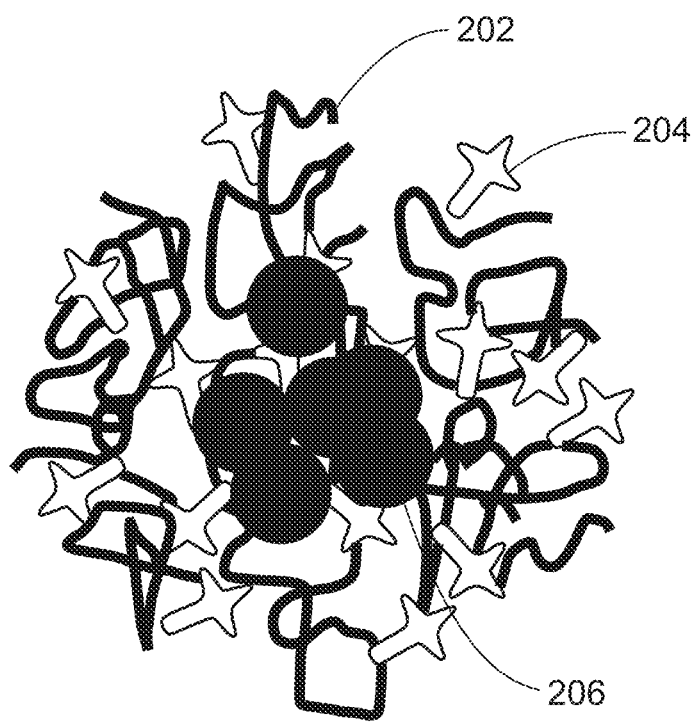
FIG. 2A shows an example of a first implementation of a fluorescent natural polysaccharide with iron oxide nanoparticles.
Figure 2B:
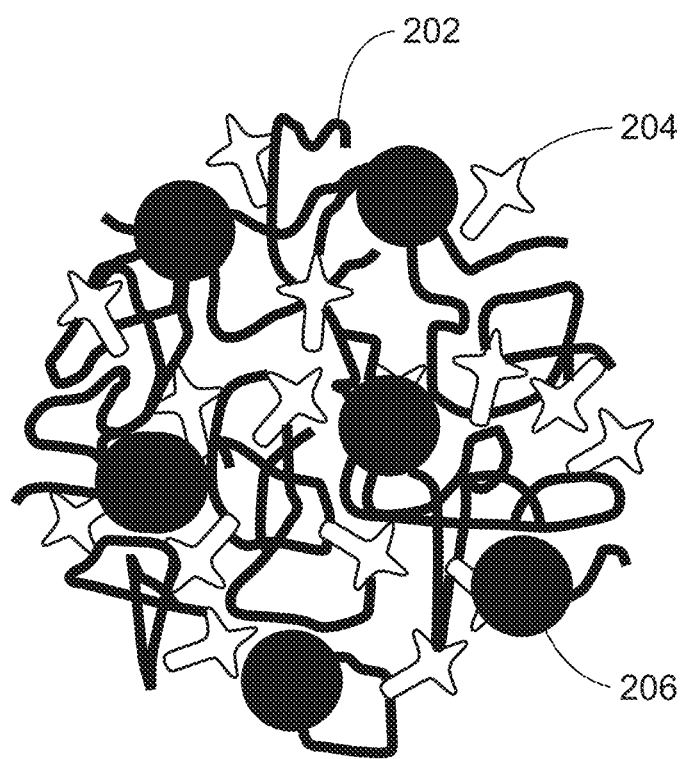
FIG. 2B shows an example of a second implementation of a fluorescent natural polysaccharide with iron oxide nanoparticles.

FIG. 2A shows an example tag 200. The tags can include natural polysaccharides 202. The natural polysaccharide forms a stable core from material that is abundantly available and inexpensive. In some implementations, the natural polysaccharide core is loaded with fluorescent dyes 204 and superparamagnetic iron oxide nanoparticles 206. Superparamagnetic iron oxide nanoparticles (SPION) are small synthetic $\gamma$-$Fe_2O_3$ or $Fe_3O_4$ particles with a core size of <15 nm. In sufficiently small nanoparticles, magnetization can randomly flip direction under the influence of temperature. This behavior allows the particles colloidal stable in suspension, while they can respond to external magnetic field. Superparamagnetic iron oxide particles (SPIONs) can be magnetized by an external magnetic field, however, SPIONs do not show magnetic interactions after the external magnetic field is removed. In some implementations, the iron oxide nanoparticles can be clustered in the center of the tag, as shown in FIG. 2A. In some implementations, the superparamagnetic iron oxide nanoparticles 206 can be randomly distributed in the tag, as shown in FIG. 2B. The fluorescent and magnetic properties allow the tag to be separated and uniquely identified.

Figure 2C:
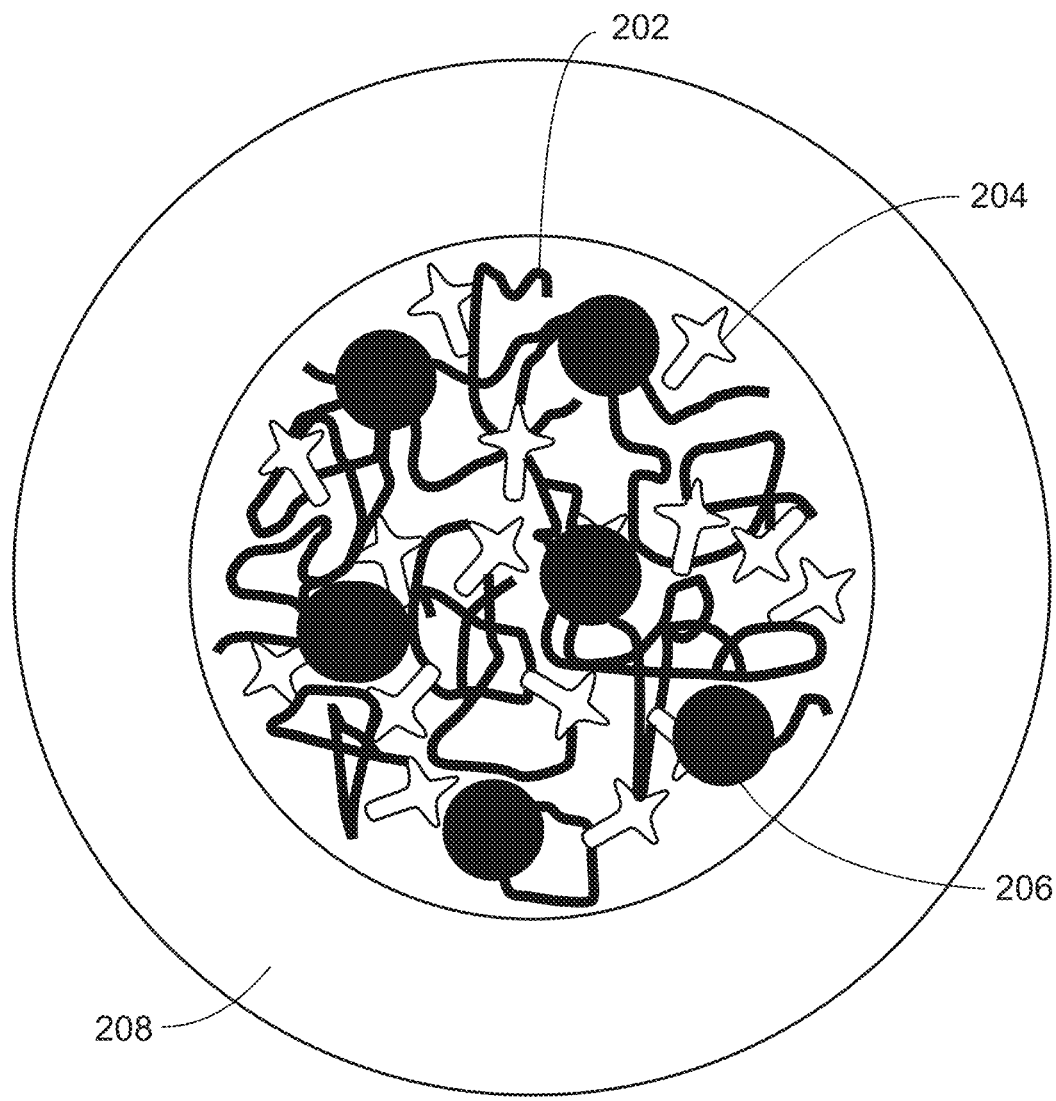
FIG. 2C shows an example of a first implementation of a fluorescent natural polysaccharide with iron oxide nanoparticles coated with a polymer shell.
Figure 2D:
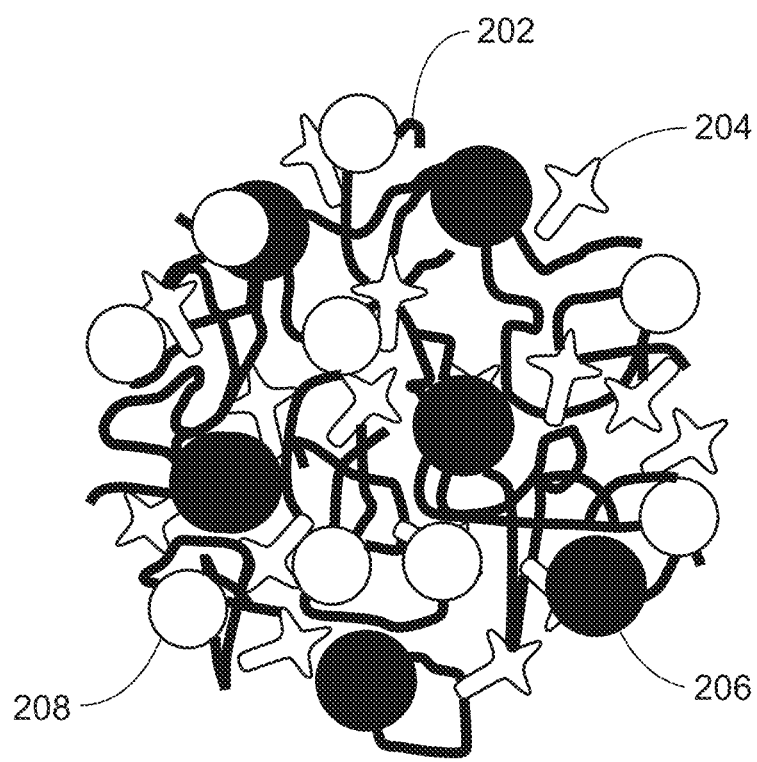
FIG. 2D shows an example of a first implementation of a fluorescent natural polysaccharide with iron oxide nanoparticles dotted with a polymer shell.

In some implementations, the tag includes a polymer shell 208, for example a thermally depolymerizable or degradable polymer. In some implementations, the polymer shell 208 encapsulates the natural polysaccharides, fluorescent dyes, and iron oxide nanoparticles, as shown in FIG. 2C. In other implementations, the polymer shell 208 is dotted on the tag, as shown in FIG. 2D. The depolymerizable or degradable polymer 208 can be used to further identify the tag or differentiate one tag from another. Advantageously, all of the components of these tags are inexpensive and environmentally friendly.

Figure 3A:
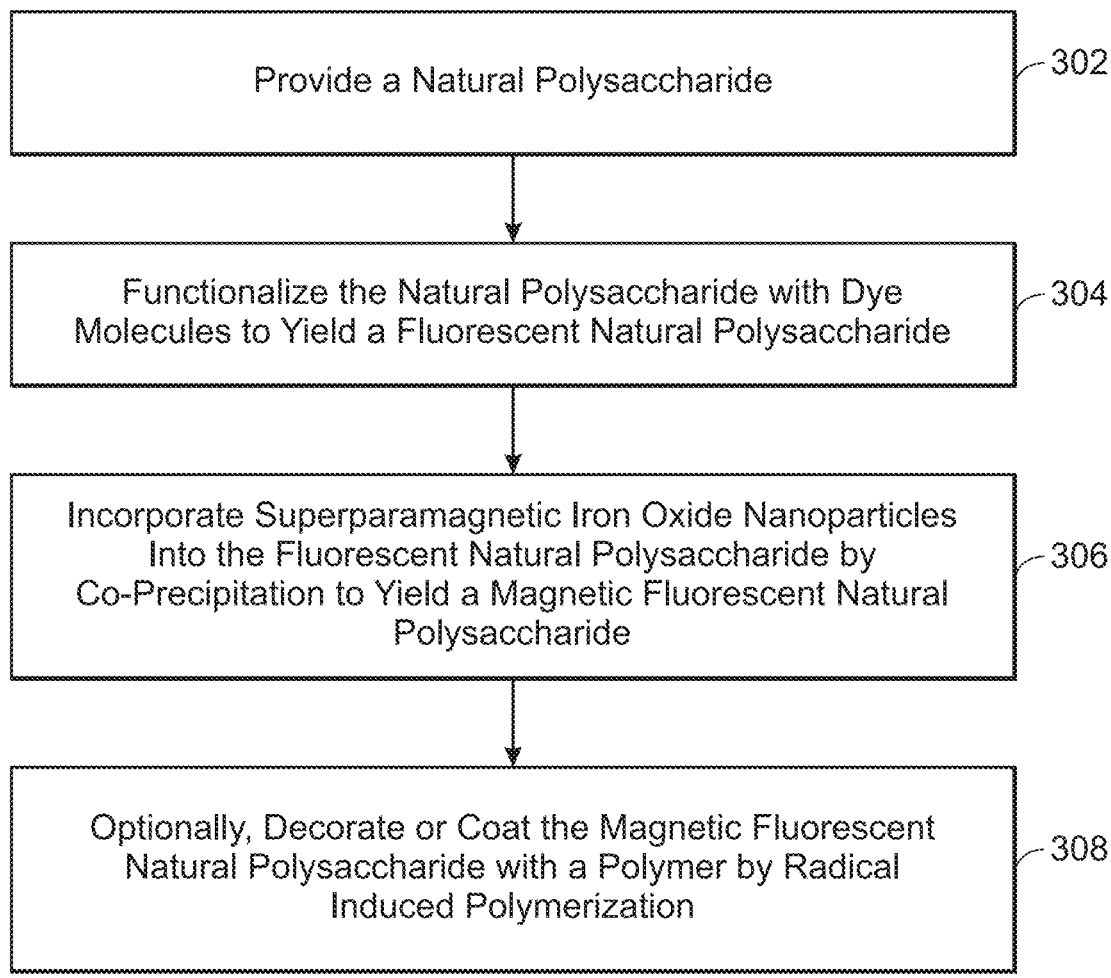
FIG. 3A shows an example schematic of a reaction scheme for functionalizing the natural polysaccharide and creating a composite nanoparticle tag.
Figure 3B:
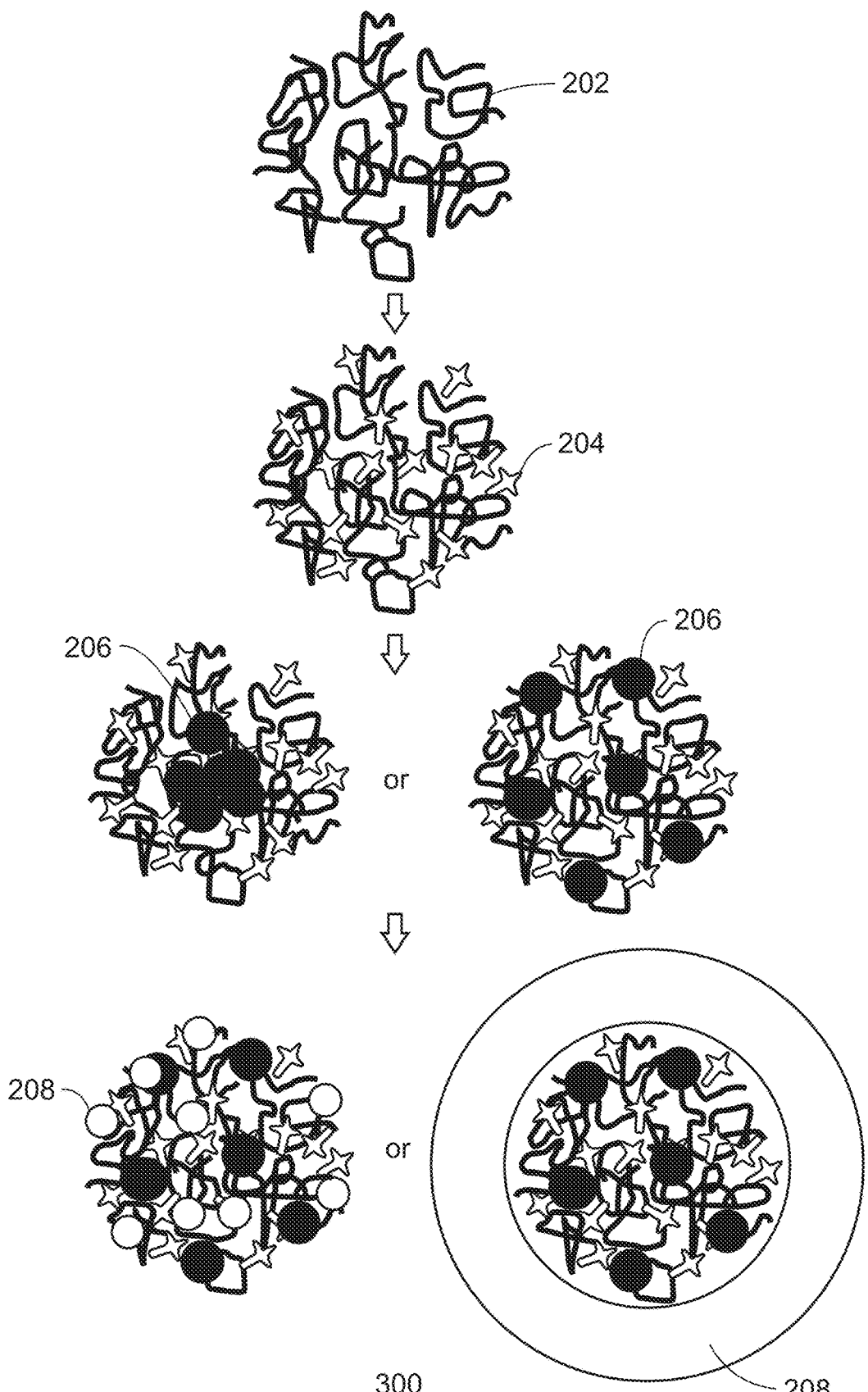
FIG. 3B shows a visual representation of the reaction scheme shown in FIG. 3A.

FIG. 3A shows an example schematic of a reaction scheme 300 for functionalizing a natural polysaccharide and creating a composite nanoparticle tag. At 302, a natural polysaccharide is provided. At 304, the natural polysaccharide is functionalized with dye molecules to yield a fluorescent natural polysaccharide (FNP). At 306, superparamagnetic iron oxide nanoparticles are incorporated into the FNP by co-precipitation to yield a magnetic FNP. Optionally, at 308, the magnetic FNP can be decorated or coated with a polymer by radical induced polymerization. FIG. 3B shows a visual representation of the reaction scheme shown in FIG. 3A.

Tags that include a natural polysaccharide core have several advantages. Natural polysaccharides are ubiquitous, abundant, and inexpensive. Further, natural polysaccharides are inherently multivalent, which enables targeted functionalization. Suitable natural polysaccharides can include chitosan, cellulose, starch, alginate, or a combination thereof.

Figure 4A:
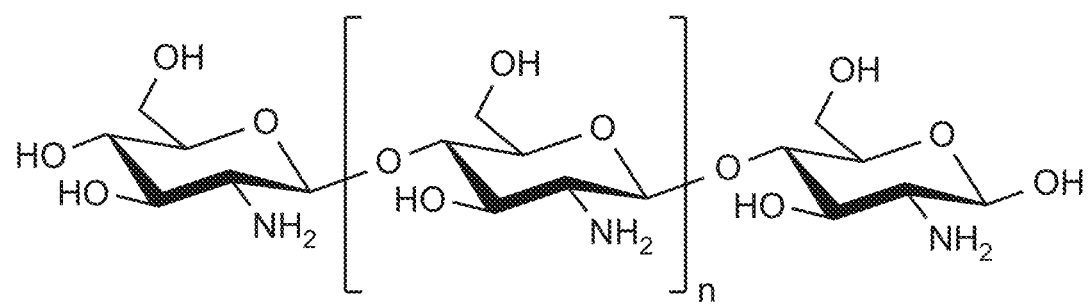
FIG. 4A shows a representative structure of chitosan.

For example, chitosan can be used as the natural polysaccharide core. Chitosan is a close derivative of poly (acetylglucosamine). Poly(acetylglucosamine) is also known as chitin. Chitin can be found in the shells of shrimp or other crustaceans, and is the second most abundant biopolymer in the world. The derivative chitosan can be made by treating chitin with an alkaline substance, for example with sodium hydroxide. Chitosan is a linear polysaccharide composed of randomly distributed $\beta$-(1→4)-linked D-glucosamine (deacylated unit) and N-acetyl-D-glucosamine (acetylated unit). FIG. 4A shows a representative structure of chitosan, with n number of repeating units.

Figure 4B:
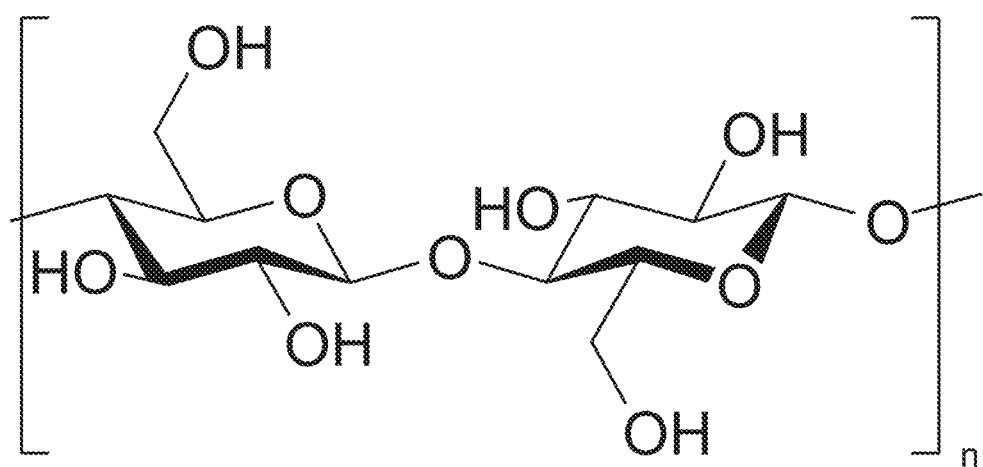
FIG. 4B shows a representative structure of cellulose.

A second suitable natural polysaccharide is cellulose, the most abundant organic polymer on earth. Cellulose is an important structural component of the primary cell wall of green plants, many forms of algae, and oomycetes. Cellulose is a polysaccharide consisting of a linear chain of several hundred to many thousands of $\beta$-(1→4) linked D-glucose units. FIG. 4B shows a representative structure of cellulose, with n number of repeating units.

Another suitable biopolymer is starch, also known as amylum. Starch is a polymeric carbohydrate that includes numerous glucose units joined by glycosidic bonds.

Figure 4C:
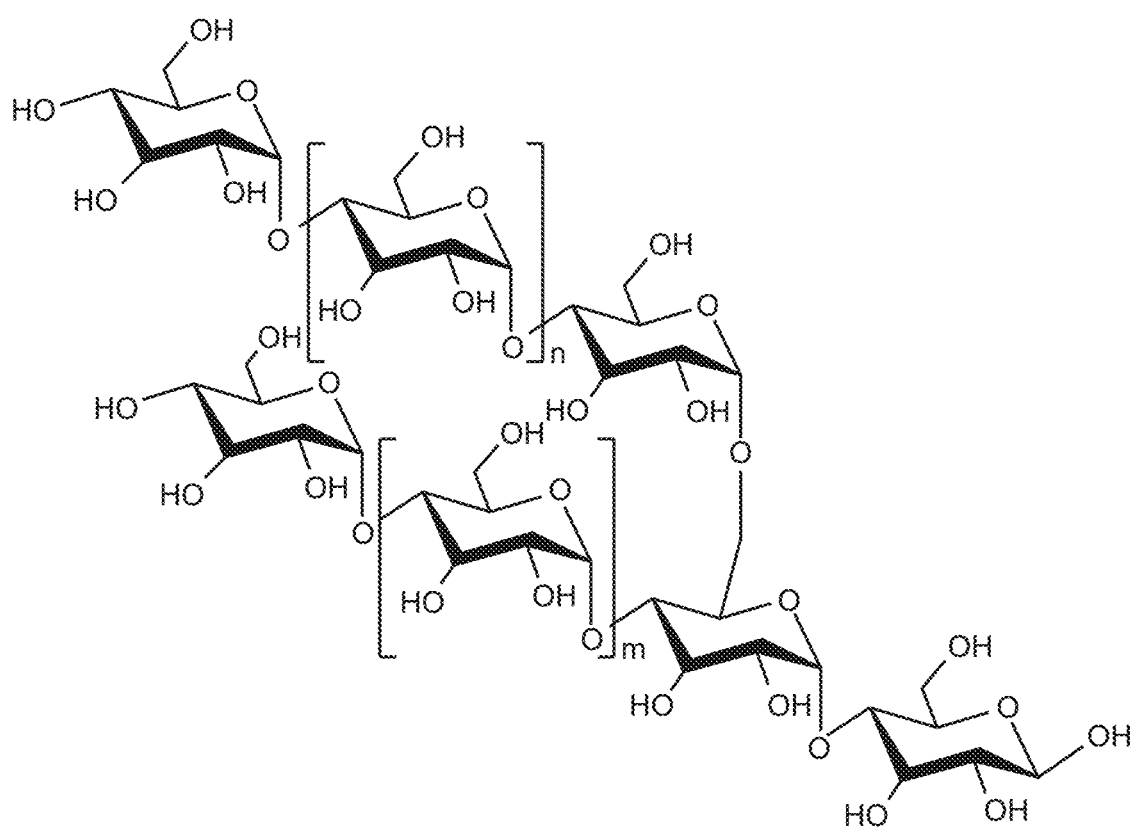
FIG. 4C shows a representative structure of starch.

Starch is produced by most green plants as energy storage. It is the most common carbohydrate in human diets and is contained in large amounts in staple food such as potatoes, corn, rice, cassava, as well as in Emmer wheat (*Triticum amyleum*). FIG. 4C shows a representative structure of starch, with n and m number of repeating glucose units joined by glycosidic bonds.

Figure 4D:
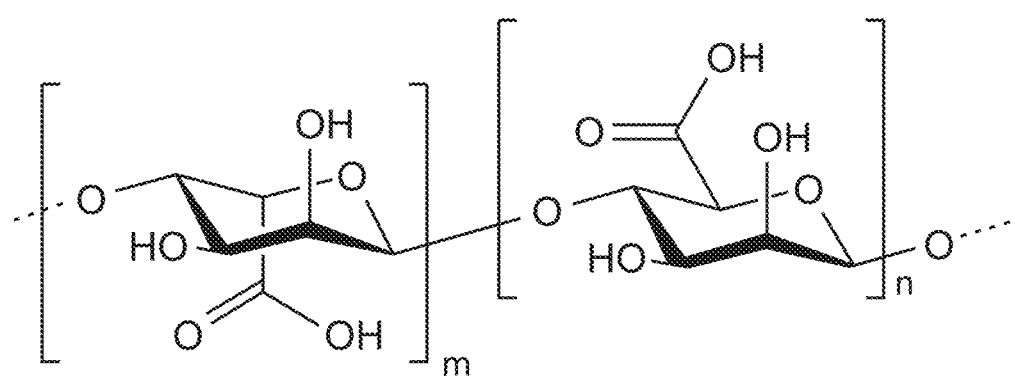
FIG. 4D shows a representative structure of alginic acid.

Alginic acid, also called algin, is a polysaccharide that is distributed widely in the cell walls of brown algae. Algin is hydrophilic and forms a viscous gum when hydrated. With metals such as sodium and calcium, algin can form salts known as alginates. FIG. 4D shows a representative structure of alginic acid. Alginic acid is a linear copolymer with homopolymeric blocks of (1→4)-linked $\beta$-D-mannuronate with n repeating units and its C-5 epimer $\alpha$-L-guluronate residues with m repeating units, covalently linked together.

Figure 5:
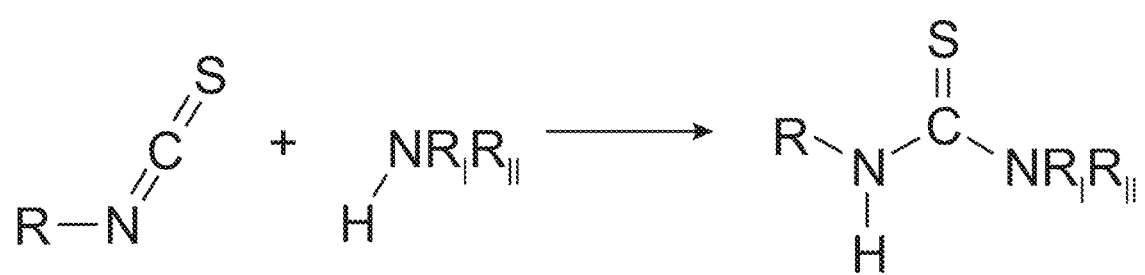
FIG. 5 shows an example reaction between an amine and an isothiocyanate to yield a thiourea.
Figure 6:
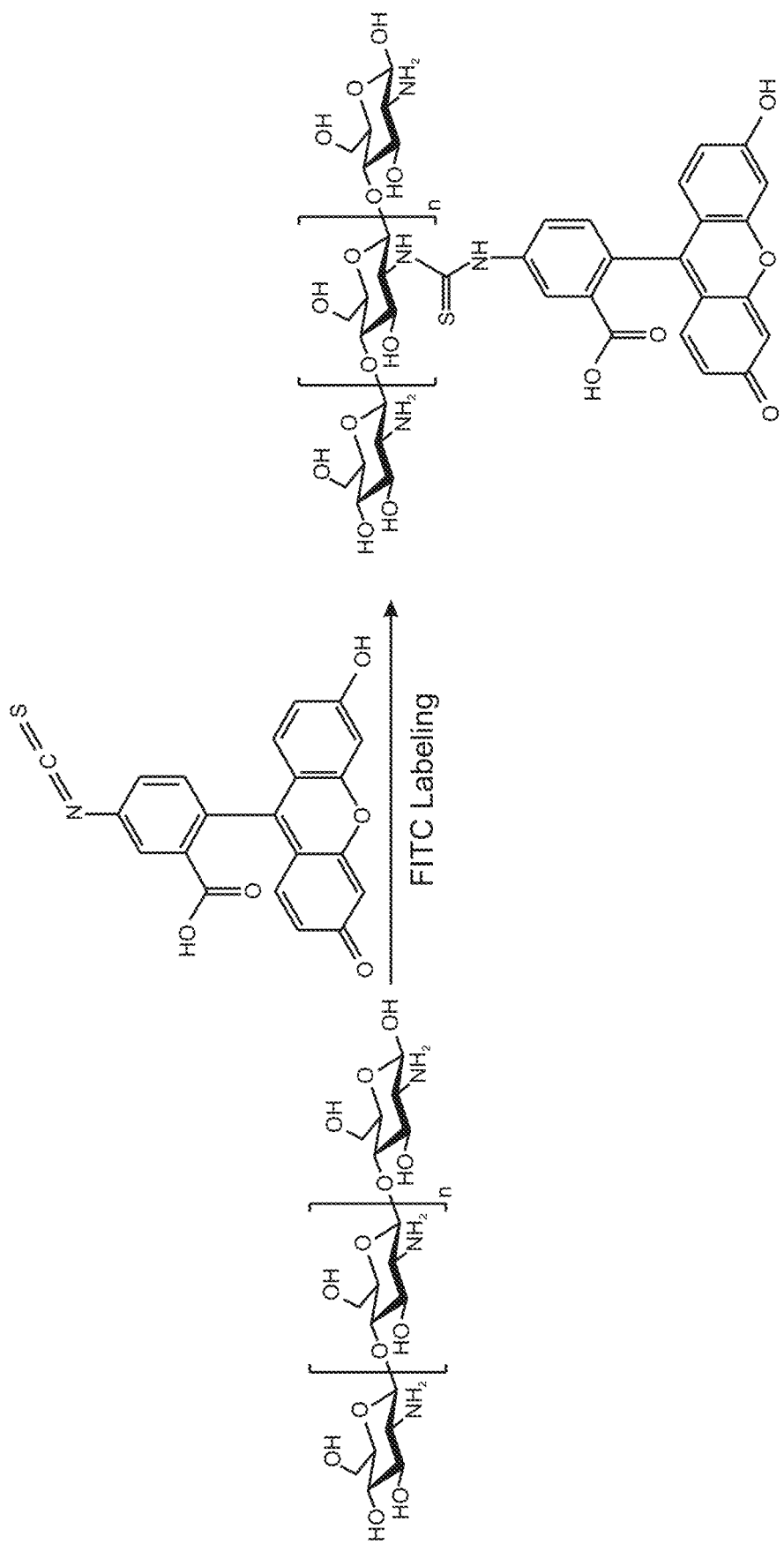
FIG. 6 shows an example reaction of chitosan with FITC to yield a fluorescent chitosan polymer.
Figure 7:
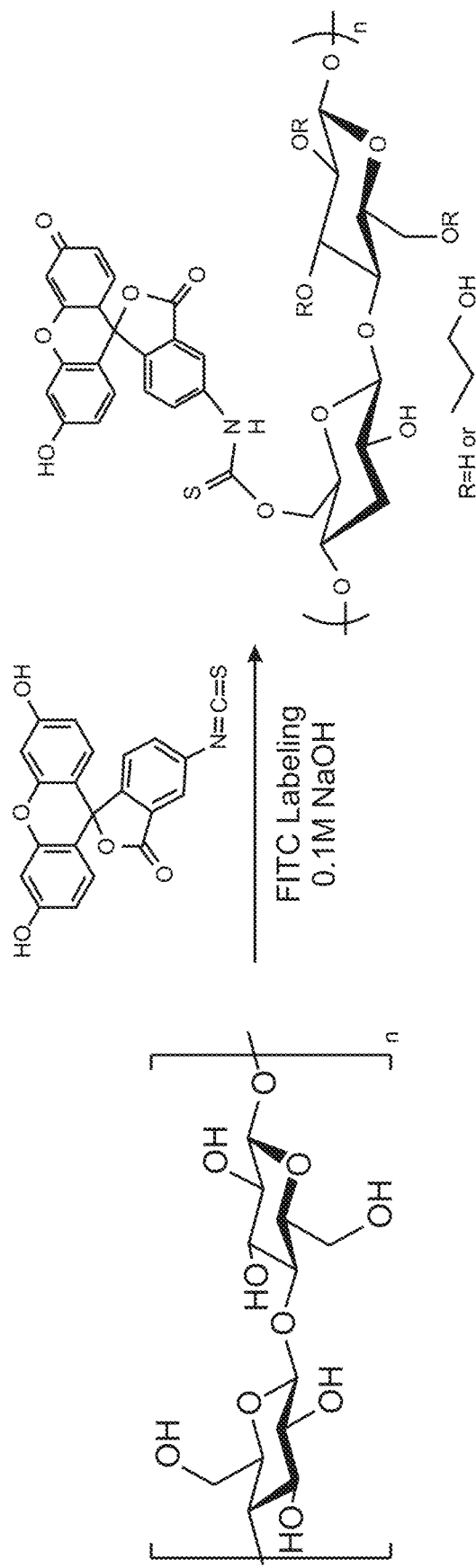
FIG. 7 shows an example reaction of cellulose with an isothiocyanate dye, FITC, under basic conditions to yield a fluorescent cellulose polymer.

In some implementations, the natural polysaccharides can be functionalized with fluorescent dyes. The fluorescent dye molecules can be grafted onto these natural polysaccharides via covalent bonds to form a fluorescent natural polysaccharide (FNP). In some implementations, the natural polysaccharide contains primary amines that can react with isothiocyanates to yield substituted thioureas. This reaction can occur at room temperature. FIG. 5 shows an example reaction between an amine and an isothiocyanate to yield a thiourea. The functional groups $R_I$ and $R_{II}$ can be H, alkyl, or aryl groups. In chitosan, there are many primary amine functional groups. Therefore, fluorescent dye molecules that contain isothiocyanate can be covalently grafted into the polymer network of chitosan, functionalizing the chitosan and yielding a fluorescent natural polysaccharide (FNP). Suitable isothiocyanate-containing fluorescent dyes include fluorescein isothiocyanate (FITC), rhodamine B isothiocyanate (RBITC), and tetramethylrhodamine isothiocyanate (TRITC). These dyes have demonstrated stability at subterranean and reservoir conditions, such as high temperatures and pressures. Accordingly, these dyes are suitable for use in drilling and wellbore operations. FIG. 6 shows an example reaction of chitosan with FITC to yield a fluorescent chitosan polymer. FIG. 7 shows an example reaction of cellulose with an isothiocyanate dye, FITC, under basic conditions to yield a fluorescent cellulose polymer.

Figure 8:
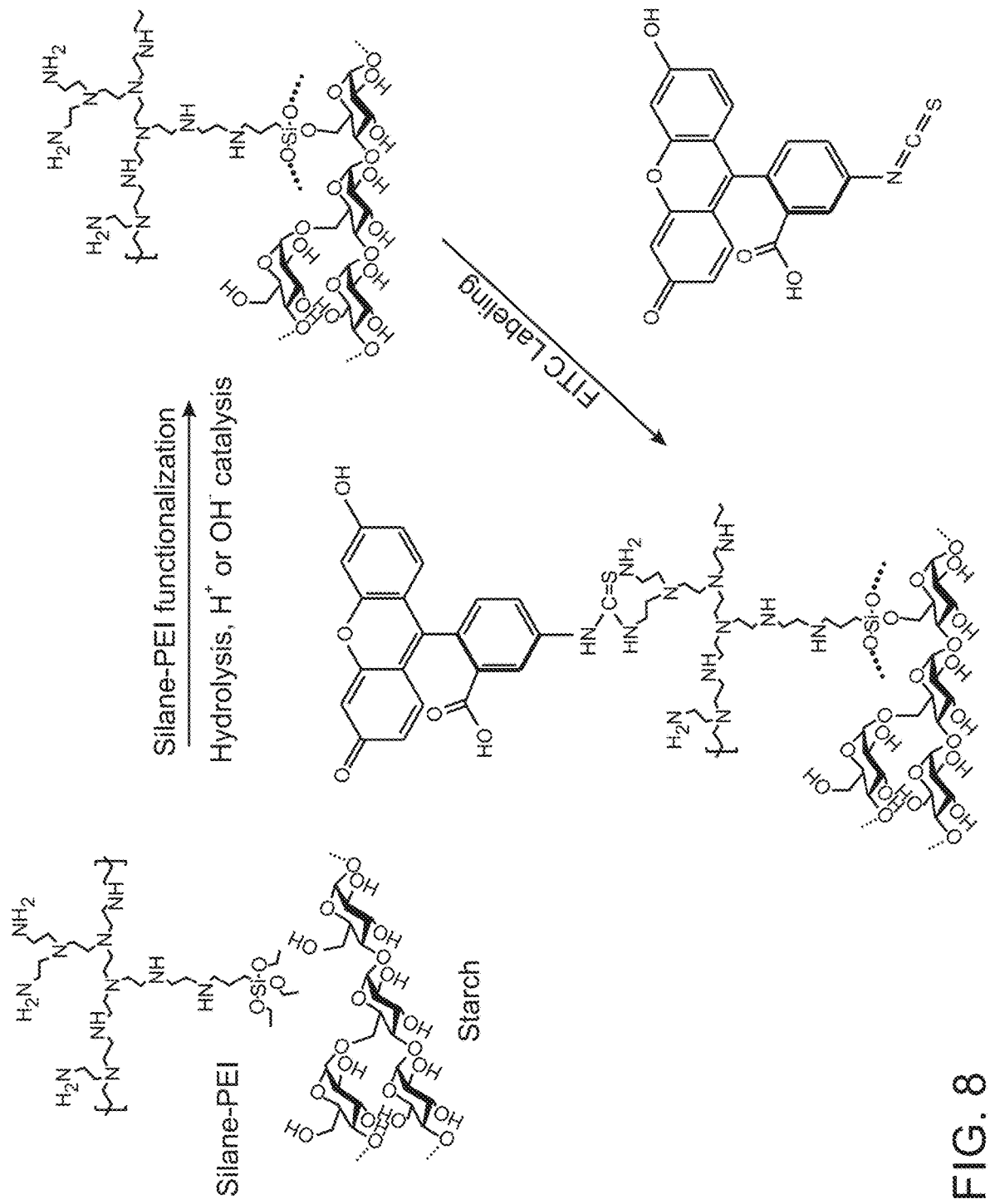
FIG. 8 shows an example reaction of starch with silane-PEI followed by a reaction with FITC to yield a fluorescent starch polymer.

Alternatively or in addition, the natural polysaccharides can be modified via hydroxyl groups, for example by reacting the naturally occurring hydroxyl groups with an amine. For example, the hydroxyl groups in starch can be modified via a reaction with silane-polyethylenimine (silane-PEI). Next, dye molecules can be linked to the imine functional groups of the silane-polyethylenimine to yield a fluorescent starch. FIG. 8 shows an example reaction of starch with silane-PEI followed by a reaction with FITC to yield a fluorescent starch polymer.

Figure 9:
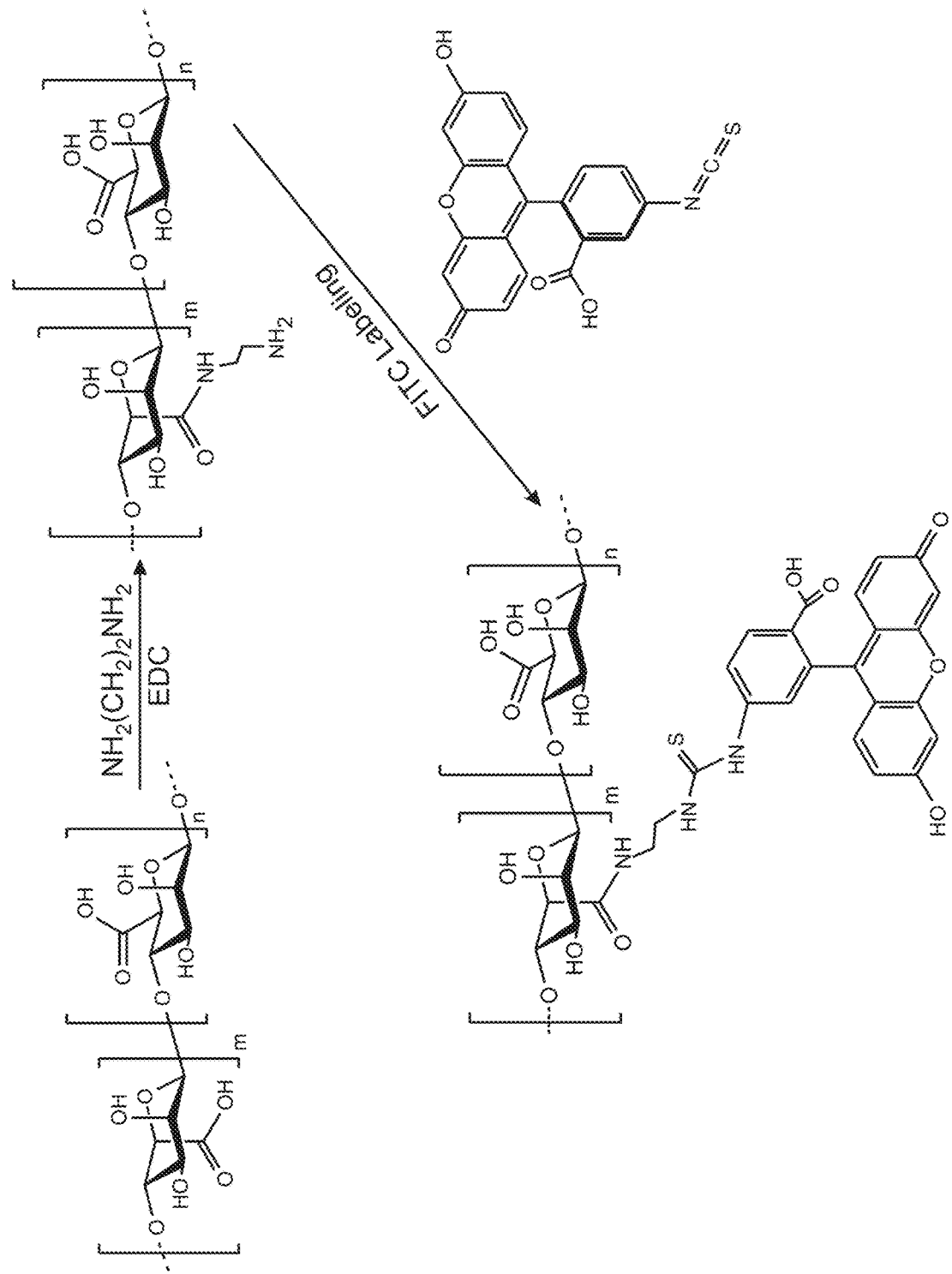
FIG. 9 shows an example reaction of alginic acid with EDC to form an o-acylisourea followed by reaction with FITC.

Isothiocyanate dyes can also be grafted onto the natural polysaccharides at basic conditions or via a reaction with 1-ethyl-3-(3-dimethylaminopropyl)carbodiimide (EDC reaction). The EDC reacts with carboxylic acid groups to form an active O-acylisourea intermediate and then reacts with primary amines to form an amide bond with the original carboxyl group. FIG. 9 shows an example reaction of alginic acid with EDC to form an o-acylisourea followed by reaction with FITC.

FIGS. 7-9 show a reaction with the isothiocyanate dye FITC, however, it is understood that any isothiocyanate-containing dye can be used in these reactions, for example RBITC and TRITC.

In some implementations, the natural polysaccharide core and/or fluorescent natural polysaccharide (FNP) is loaded with superparamagnetic nanoparticles, for example superparamagnetic iron oxide nanoparticles. These superparamagnetic iron oxide nanoparticles can be formed in situ and attached to a natural polysaccharide or a dye functionalized FNP. When the primary size of magnetic iron oxide nanoparticles is less than 15 nm, the nanoparticles exhibit superparamagnetism. Superparamagnetic iron oxide particles (SPIONs) can be magnetized by an external magnetic field, however, SPIONs do not show magnetic interactions after the external magnetic field is removed. SPIONs can be formed by co-precipitation of ferric and ferrous ions in solution by reaction with a base. Equation 1 shows an example co-precipitation reaction:

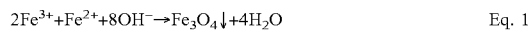

$$2Fe^{3+}+Fe^{2+}+8OH^{-} \rightarrow Fe_3O_4\downarrow+4H_2O \qquad \text{Eq. 1}$$

When SPIONs are synthesized in the presence of fluorescent natural polysaccharides (FNPs), the resulting SPIONs are attached to the natural polysaccharides to yield magnetic FNPs. The iron oxide nanoparticles have strong sorption on natural polymers. The magnetic FNPs can be separated and collected from a suspension or mixture by a strong magnet, for example by a neodymium (NdFeB) magnet.

In some implementations, the FNPs and/or magnetic FNPs can be coated with a thermally depolymerizable or degradable polymer coating. For example, monomer molecules can be dissolved in water in presence of FNPs and/or magnetic FNPs, and then the polymerization reaction occurs by adding an initiator to the suspension, yielding nanoparticles that are coated by the polymer. In some implementations, the initiator is $Na_2S_2O_8$ or $(NH_4)_2S_2O_8$. In some implementations, the magnetic FNPs can be coated with polystyrene or a polystyrene based polymer. Styrene based polymers cleanly decompose into their constituent monomers at elevated temperatures. Accordingly, the entire polymer mass contributes to the generation of detectable units, maximizing atom economy. The constituent monomers can be identified and therefore the polymer coating can be identified. Unique combinations of unique monomers can be used to create a plurality of polymer coatings that can be differentiated by mass spectrometry. In other words, using different monomers as starting materials for the polymer coatings, the resulting polymer shells carry different "barcode" information and enable unique identification of their original monomer structures. For example, the constituent monomers of the polymer can be determined by pyrolysis-gas chromatography-mass spectrometry (pyrolysis-GC-MS) analysis or by gas chromatography-flame ionization detection/mass spectrometry (GC-FID/MS). The polymer can include monomers derived from styrene, p-methylstyrene, p-methoxystyrene, 2,4-dimethyl styrene, 2,4,6-trimethylstyrene, 4-chlorostyrene, or 4-bromostyrene, or any combination thereof.

In some implementations, the polymer can include monomers derived from phenyl methacrylate, hexyl methacrylate, or butyl methacrylate, or any combination thereof.

In some implementations, the polymer shell fully encapsulates the multifunctional core. Alternatively, in some implementations the polymer shell does not fully encapsulate the multifunctional core. Brush-like or dot-like decoration of styrene-based polymers on to the magnetic FNP can likewise result in a tag that can be identified by the unique monomers present in the styrene-based polymer. Brush-like or dot-like decoration can result in a polymer coating that is a continuous thin layer or a polymer coating that is in discrete patches.

Fluorescence spectroscopy has demonstrated that the FNPs exhibit strong fluorescence, and that the inclusion of SPIONs and polystyrene coatings does not significantly quench or suppress the fluorescence from the dye molecules. Accordingly, these tags are detectable by fluorescence analysis.

The natural polysaccharide based tags mix well with drilling mud, and there is no phase separation observed in a mud-tag mixture for up to months at a time. Accordingly, the tags can be used in combination with drilling mud to tag rock cuttings or subterranean rock samples. The tags are suitable for use in both oil-based and water-based mud.

For example, the tags can be mixed with the drilling mud and flowed or pumped down a work string into a subterranean formation. The mud and tag mixture exits the work string at the drill bit. Accordingly, the tags come into contact with the subterranean formation for the first time as they exit the drill bit. The tags can embed into or decorate the subterranean formation and the rock cuttings produced by the drill, for example, through physical sorption on a rock surface. The drilling mud carries the rock cuttings to the surface of the wellbore, where they can be recovered and analyzed.

In some implementations, the tagged rock cuttings or rock samples are separated from the untagged rock samples using a magnet. Advantageously, this also pre-concentrates the tagged rock samples, and reduces the number of samples that need to be subsequently analyzed. In some implementations, the magnetic properties of the tag can be used to separate unbound tags from drilling mud. Accordingly, these tags can be removed from the mud for re-use. Further, the mud can be used again, either without tags or with a new tag. This prevents residual tags from contributing to background signals or interfering with subsequent drilling operations.

The identity of the tags can be determined by a number of techniques, including fluorescent analysis and mass spectrometry. Fluorescent analysis can be used to determine the identity of the fluorescent dye present in the FNP by fluorescence imaging or spectroscopy. The fluorescence images can be taken by camera system under UV or visible light excitation, while the fluorescence spectra can be recorded by a portable spectroscopic system on site. In some implementations, the fluorescent analysis can occur at the wellbore or drilling site. The fluorescent analysis can provide a first set of real-time data about the tags and rock cuttings. This data can be used to make subsequent decisions about drilling operations. Alternatively or in combination, the tags can be analyzed with mass spectrometry, for example pyrolysis-gas chromatography-mass spectrometry or gas chromatography—FID/MS, as described herein. In some implementations, the mass spectrometry analysis can be done at the wellbore or drilling site. In other implementations, the mass spectrometry analysis occurs off-site, for example in a laboratory.

The tags described herein can be engineered with unique fluorescence and mass spectrometry signals, as described in detail above. Accordingly, different combinations of different fluorescence and mass spectrometry signals can create a library of uniquely identifiable tags. In some implementations, a first tag can be introduced to a subterranean formation at a first time point, and a second tag can be introduced to a subterranean formation at a second time point. Therefore, when the position of the drill bit and the lag time of the tags as they travel down the work string is known, rock cuttings or subterranean rock samples tagged with a first tag can be assigned a first origin location, and subterranean rock samples tagged with a second tag can be assigned to a second origin location. The number of tags is not limited to two, and a plurality of tags can be used to assign a plurality of origin locations.

Figure 10:
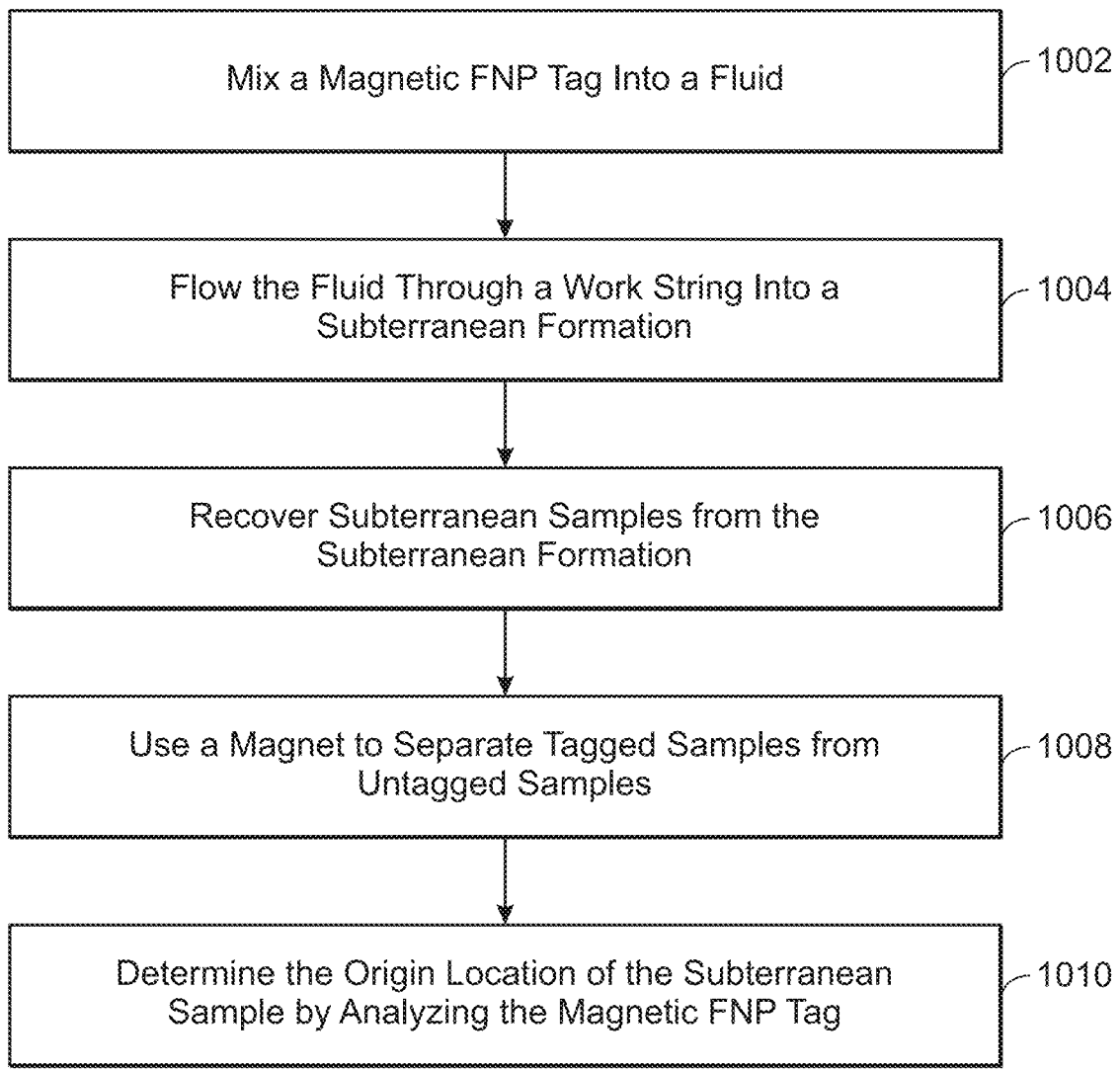
FIG. 10 shows a flowchart of an example method of determining the origin location of a subterranean rock cutting produced during drilling.

FIG. 10 shows a flowchart of an example method 1000 of determining the origin location of a subterranean rock cutting produced during drilling. At 1002, a magnetic FNP tag is mixed into a fluid. At 1004, the fluid is flowed through a work string into a subterranean formation. At 1006, subterranean rock samples are recovered from the subterranean formation. At 1008, a magnet is used to separate tagged rock samples from untagged rock samples. At 1010, the origin location of the subterranean rock sample is determined by analyzing the magnetic FNP tag.

Example 1—Fluorescent Labeling of Chitosan

Figure 11:
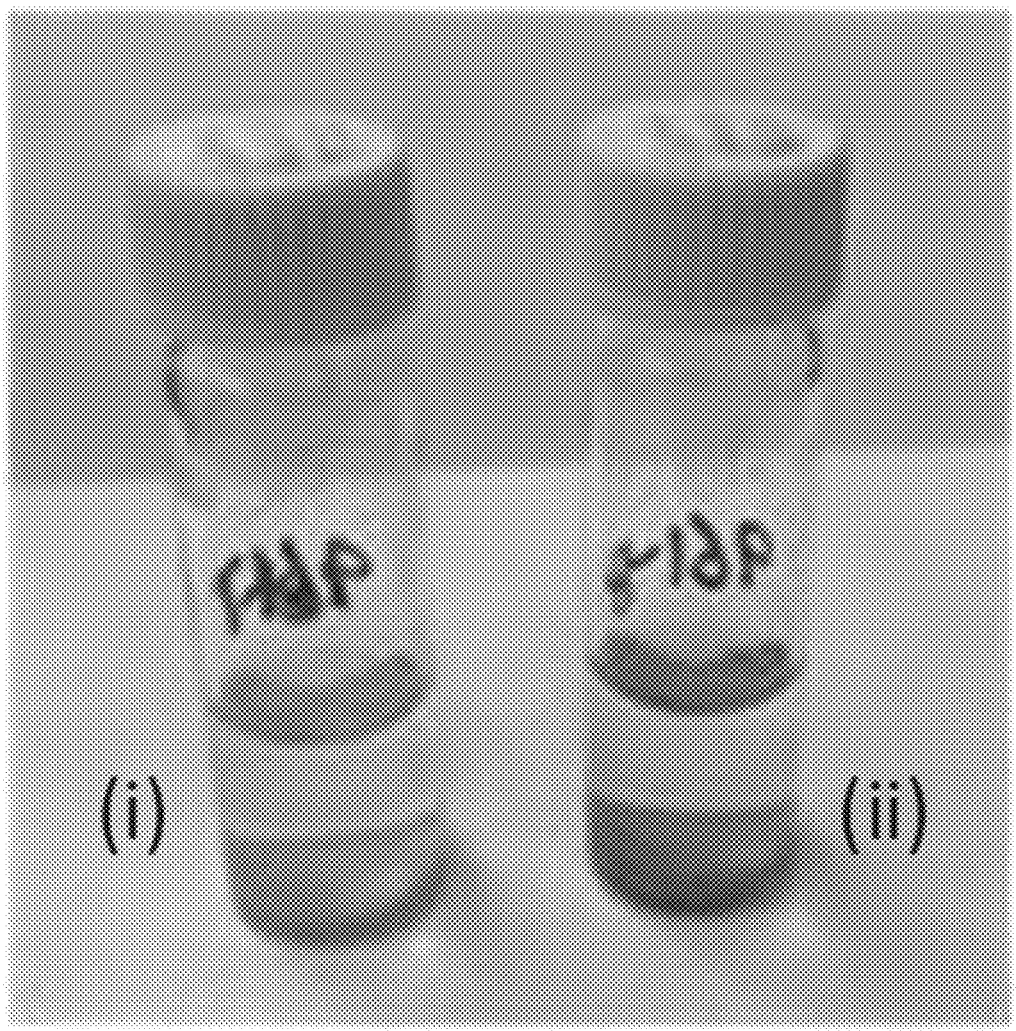
FIG. 11 shows an example photograph of chitosan labeled with FITC and RBITC.
Figure 12:
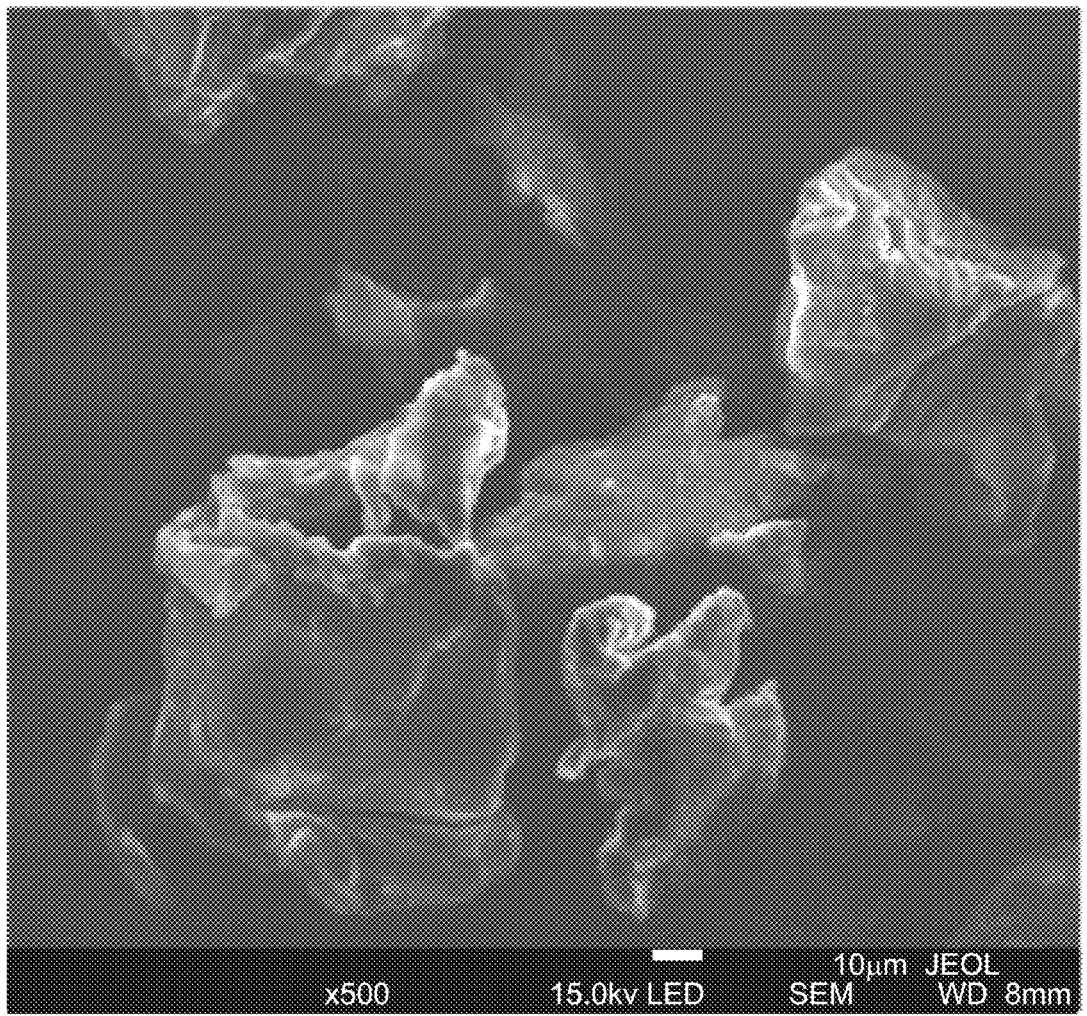
FIG. 12 shows an example SEM image of chitosan functionalized with FITC.

For the synthesis of fluorescently labeled chitosan, chitosan 1.0 g (medium molecular weight) was dispersed in 100 mL deionized (DI) water, and 10 mg of FITC dye or RBITC dye was dissolved into 50 mL water-ethanol (9:1) mixture, respectively, and then the chitosan and dye mixed and react for 6 hours under stirring. Upon completion of the reaction, the dye molecules are grafted onto chitosan (containing 1 wt % of dye). The chitosan particles labelled by dye were separated by centrifugation. FIG. 11 shows an example photograph of chitosan labeled with FITC (i) and RBITC (ii). FIG. 12 shows an example SEM image of chitosan functionalized with FITC.

Example 2—Inclusion of SPIONs in Fluorescent Chitosan

For the synthesis of SPIONs in fluorescent chitosan, in 150 mL chitosan-FITC or chitosan-RBITC from Example 1, 8.1 g $FeCl_3.6H_2O$ and 4.2 g $FeSO_4.7H_2O$ were dissolved under $N_2$ atmosphere, giving 2:1 molar ratio of $Fe^{3+}/Fe^{2+}$. Next, 7.5 mL of 29.5 wt % ammonia solution was added dropwise at a rate of 2.5 mL/min into the solution under vigorous stirring. With the addition of ammonia solution, magnetite ($Fe_3O_4$) nanoparticles formed immediately, and the solution turns to black and viscous and then to deep brown and becomes more fluid. The reaction was allowed to continue at room temperature for 2 hours to ensure the formation of chitosan-dye-$Fe_3O_4$ composites. The chitosan-dye-$Fe_3O_4$ composite particles can be separated from solution by a magnet. The weight ratio of chitosan-dye to magnetic $Fe_3O_4$ in the composite is about 1:2, although the ratio is adjustable. The samples, casted film on silicon wafer, were imaged by scanning electron microscopy (JEOL 7100 TFE SEM) operated at 15 kV voltage.

Figure 13:
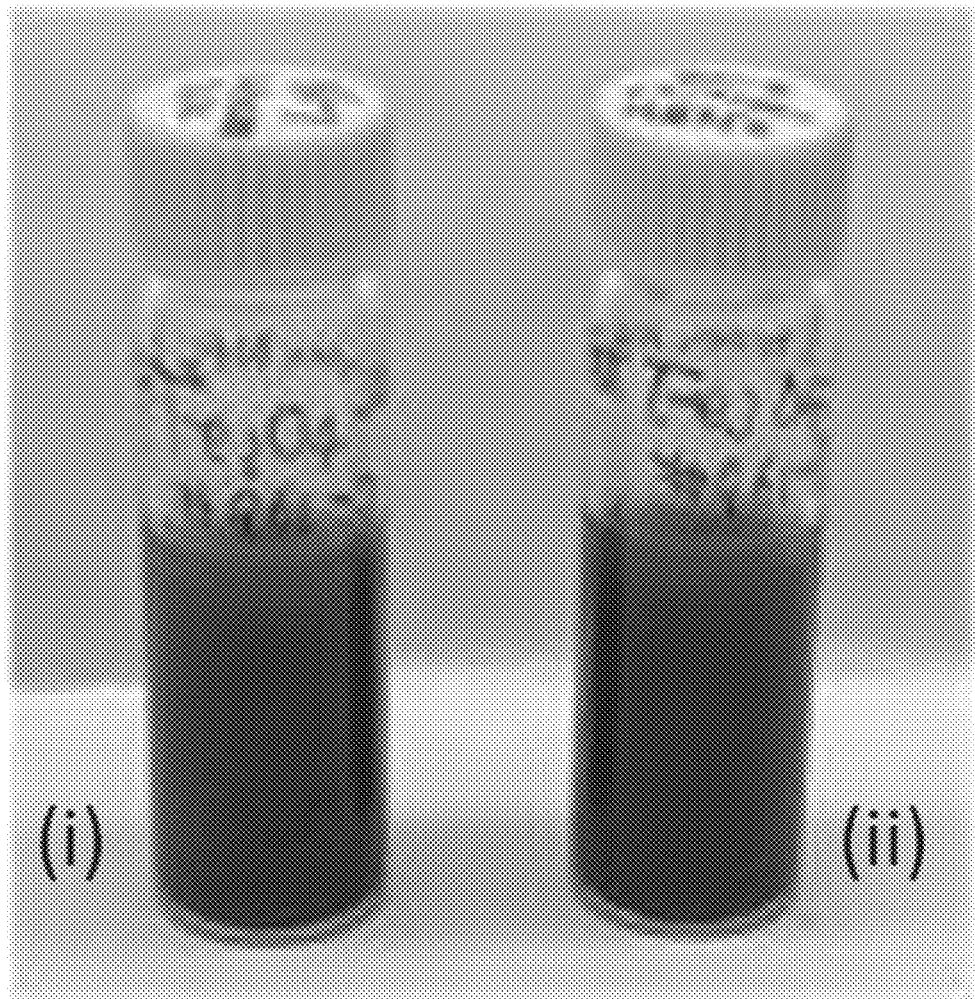
FIG. 13 shows an example photograph of the chitosan functionalized with FITC and RBITC with attached superparamagnetic $Fe_3O_4$ nanoparticles in suspension.
Figure 14:
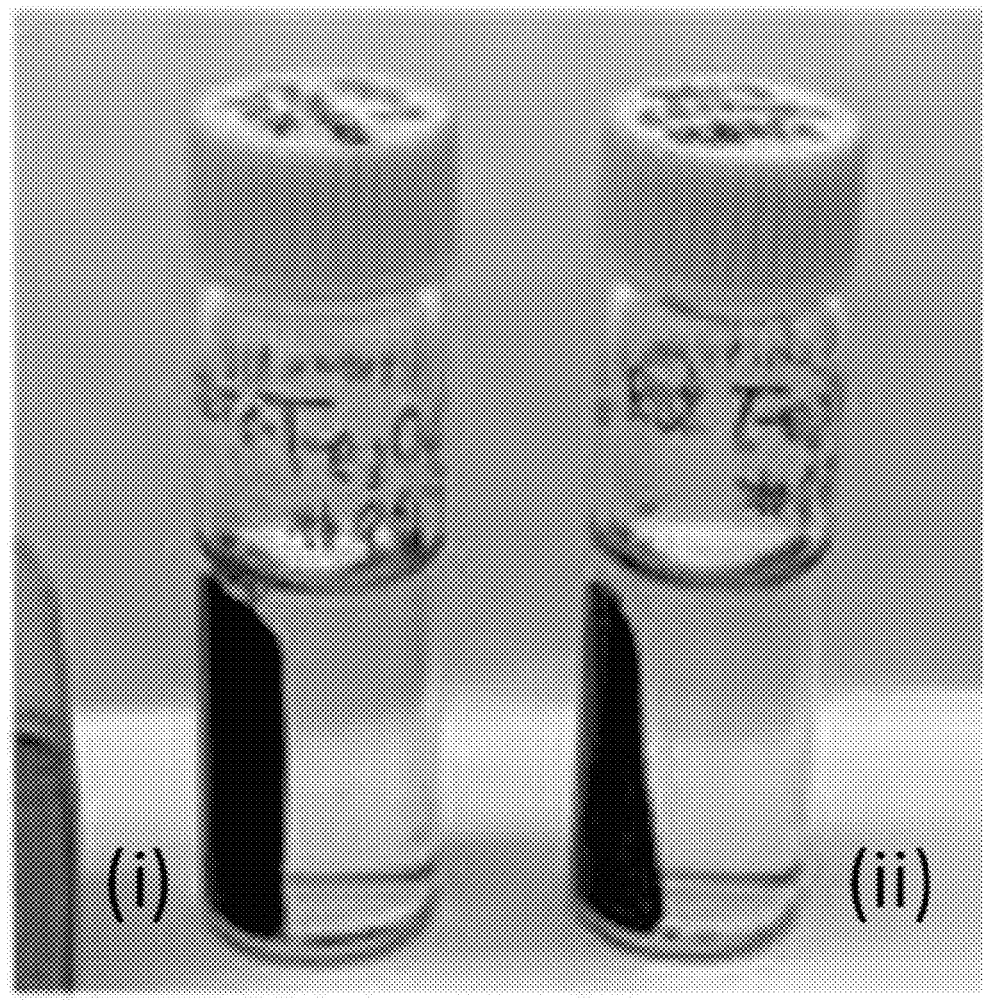
FIG. 14 shows an example photograph of the chitosan-dye-$Fe_3O_4$ complexes magnetically separated by an external magnet.
Figure 15:
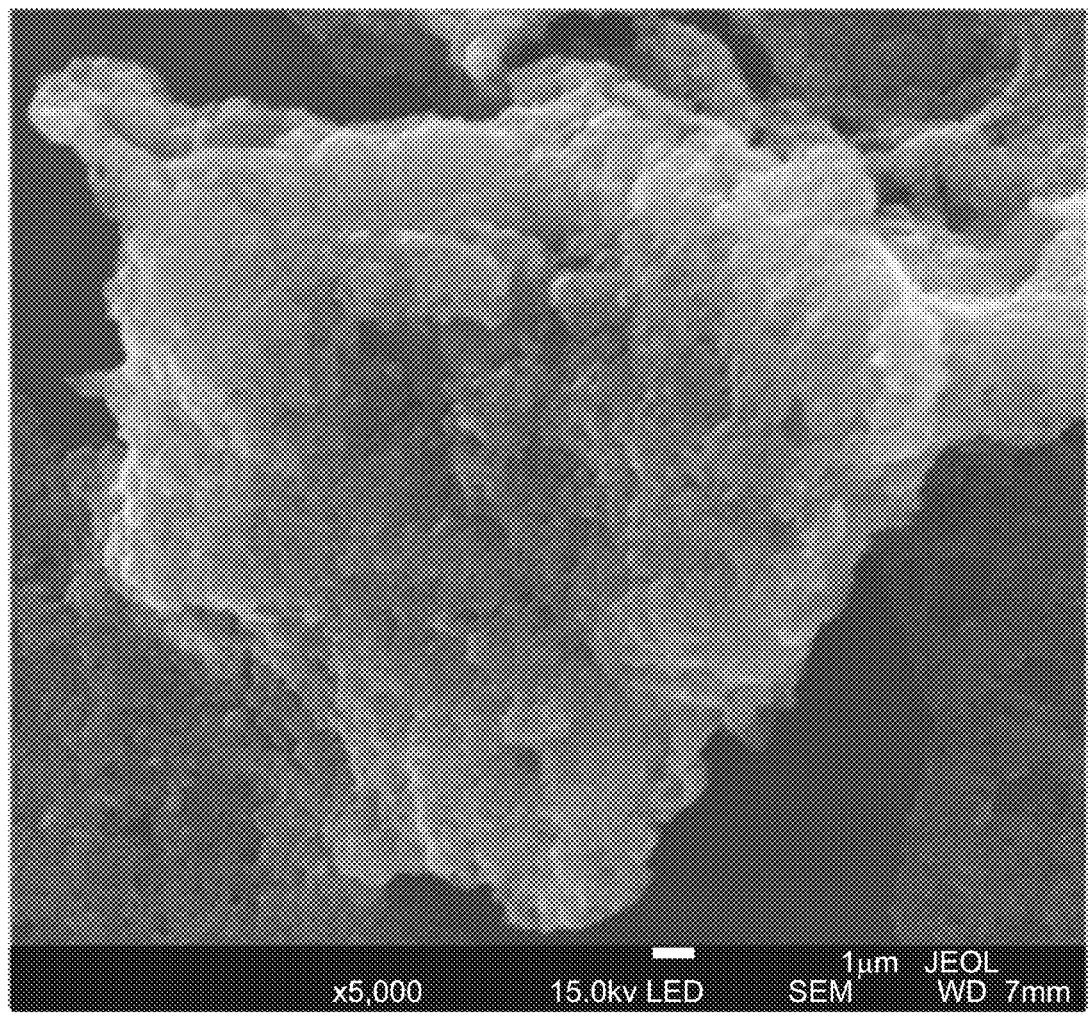
FIG. 15 shows an example SEM image of chitosan labeled with FITC and $Fe_3O_4$ nanoparticles.

FIG. 13 shows an example photograph of chitosan functionalized with FITC (i) and RBITC (ii) with attached superparamagnetic $Fe_3O_4$ nanoparticles in suspension. FIG. 14 shows an example photograph of the chitosan-dye-$Fe_3O_4$ complexes (i) and (ii) magnetically separated by an external magnet. FIG. 15 shows an example SEM image of chitosan labeled with FITC and $Fe_3O_4$ nanoparticles.

Example 3—Polystyrene Coating of SPION/Fluorescent Chitosan

Figure 16:
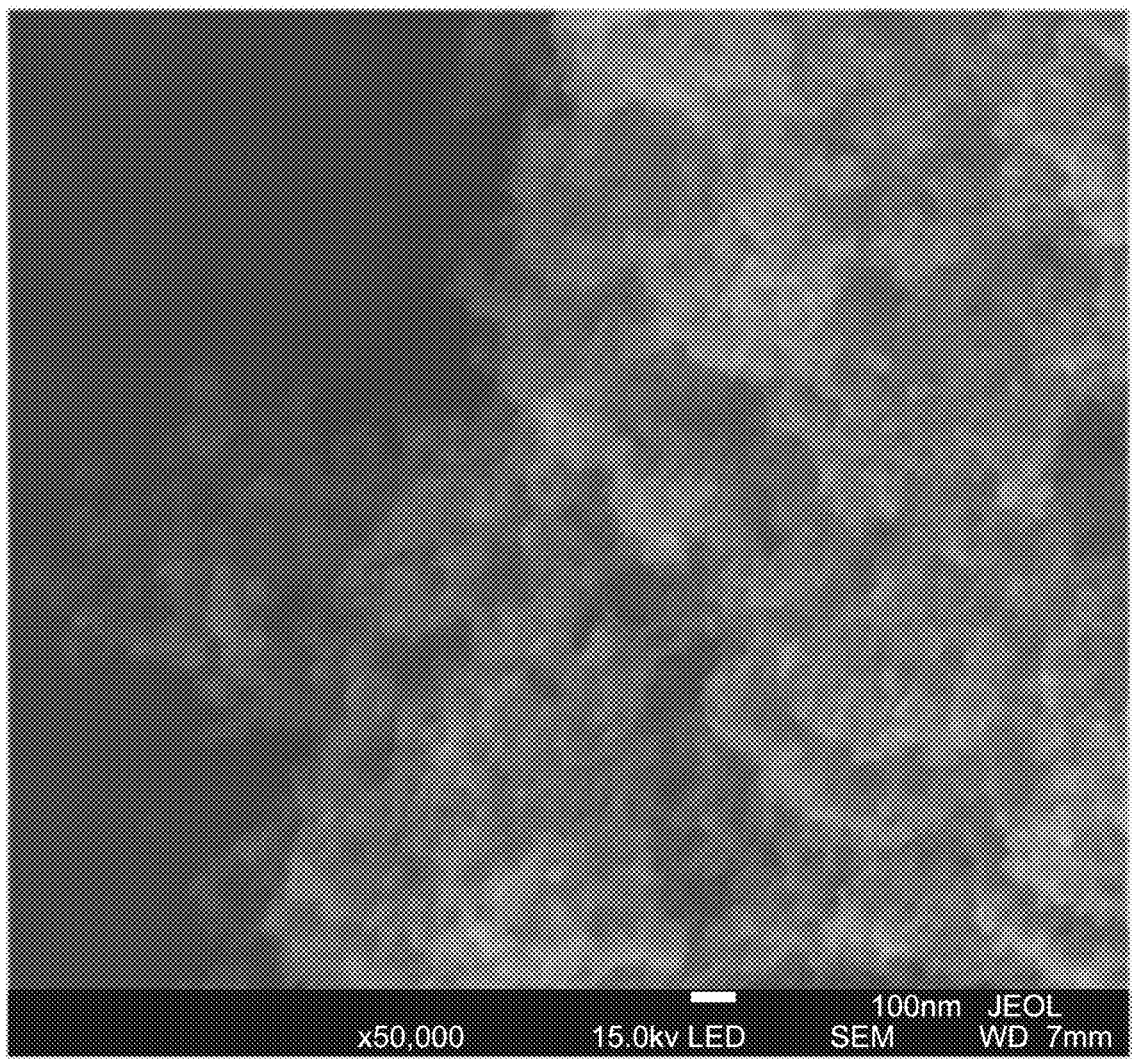
FIG. 16 shows an example of chitosan-FITC-$Fe_3O_4$ coated with polystyrene.

To coat the chitosan-FITC-$Fe_3O_4$ or chitosan-RBITC-$Fe_3O_4$ composite particles, the above collected composite particles were redispersed in 150 mL 0.25 wt % sodium dodecyl sulfate (SDS) solution. 2.5 mL styrene was added and the mixture was stirred for 2 hours to allow adsorption of the styrene on the particles. Then, 0.2 g ammonium persulfate was added and the reaction mixture was heated to 70° C. for 2 hours. The resulting chitosan-FITC-$Fe_3O_4$—PS or chitosan-RBITC-$Fe_3O_4$—PS composite particles were separated and collected form solution by a magnet. FIG. 16 shows an example SEM image of chitosan-FITC-$Fe_3O_4$ coated with polystyrene.

Example 4—Fluorescence of Modified Chitosan

Figure 17:
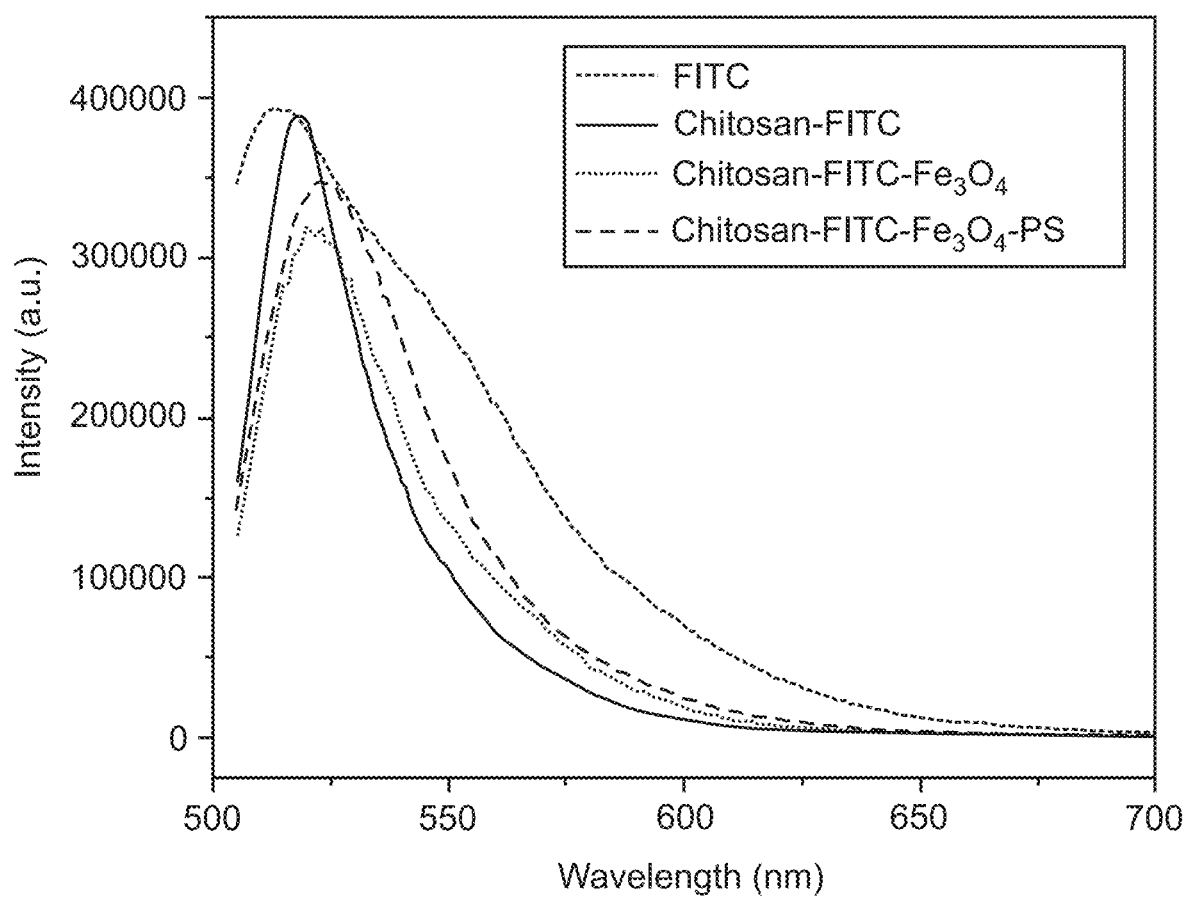
FIG. 17 shows an example fluorescence spectrum of FITC, as well as modified chitosan polymers chitosan-FITC, chitosan-FITC-$Fe_3O_4$, and polystyrene-coated chitosan-FITC-$Fe_3O_4$—PS.

FIG. 17 shows an example fluorescence spectrum of FITC, as well as modified chitosan polymers chitosan-FITC, chitosan-FITC-$Fe_3O_4$, and polystyrene-coated chitosan-FITC-$Fe_3O_4$—PS. The spectra were measured with a Horiba NanoLog-3 fluorescence spectrometer, and the concentration of samples was approximately 1 wt % in water suspension. As shown in FIG. 17, the inclusion of chitosan, $Fe_3O_4$, and polystyrene does not significantly alter the fluorescence signal of FITC. Accordingly, the modified chitosan polymers can exhibit fluorescent signals and can be used as fluorescent tags in wellbore and subterranean applications.

Example 5—Fluorescent Labeling of Starch

Figure 18:
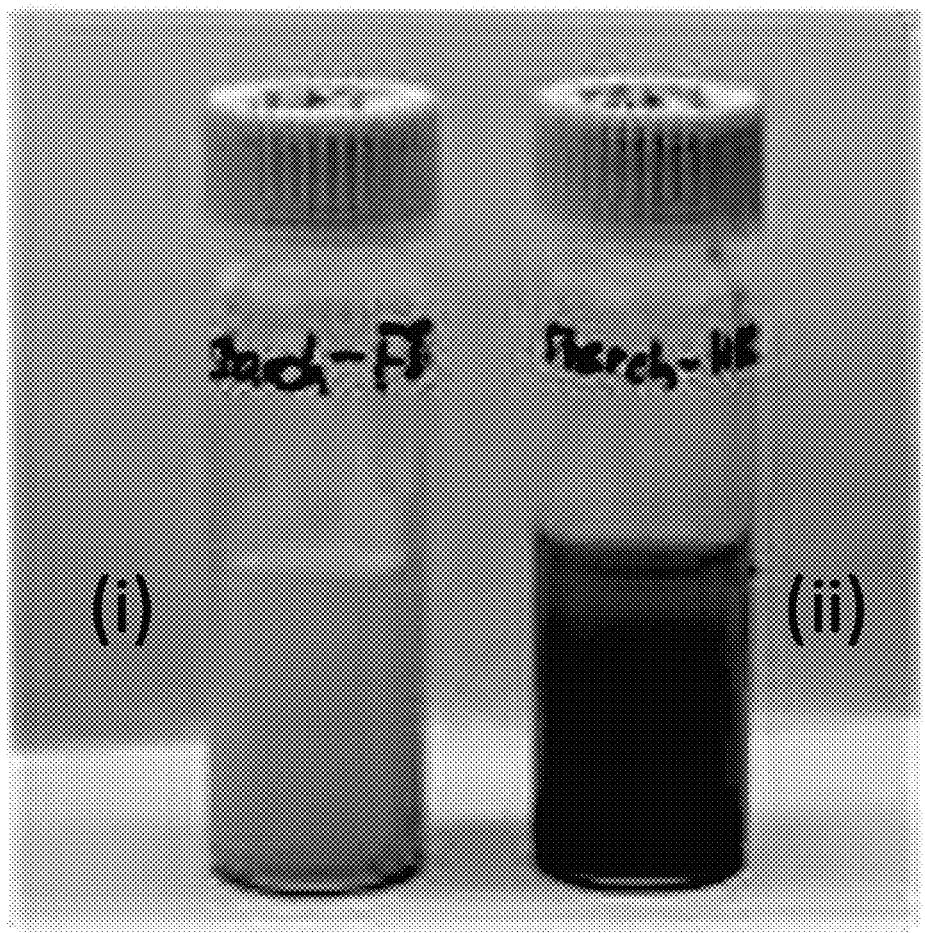
FIG. 18 shows an example photograph of starch functionalized with FITC and RBITC.
Figure 19:
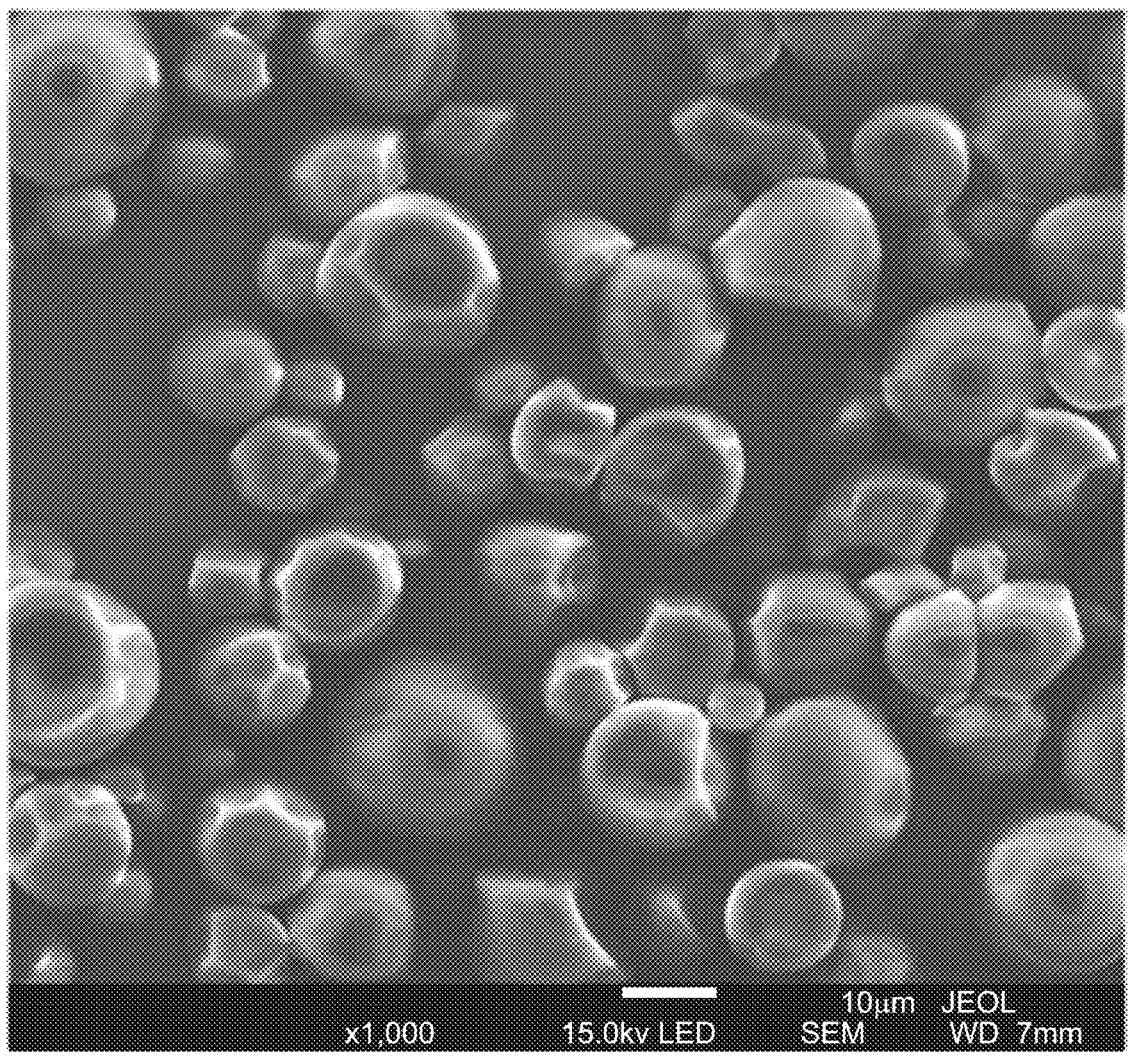
FIG. 19 shows an example SEM image of starch functionalized with RBITC.

For the fluorescent labeling of starch, 1.0 g starch (from potato) was dispersed in 100 mL DI water and 2 mL$NH_3·H_2O$ (29.5 wt %) was added. After stirring the starch dispersion for 2 hours, 50 mL ethanol with 1 mL dissolved polyamine, trimethoxysilylpropyl modified (polyethylenimine) (Gelest, 50% in isopropanol), was added under stirring. After 12 hours, 10 mg dye FITC or RBITC was added to the reaction mixture and the reaction continues for additional 6 hours. Upon completion of the reaction, the dye molecules are grafted onto starch, and the starch particles labelled by dye were separated by centrifugation. FIG. 18 shows an example photograph of starch functionalized with FITC (i) and RBITC (ii). FIG. 19 shows an example SEM image of starch functionalized with RBITC.

Example 6—Incorporation of SPIONs in Fluorescent Starch

Figure 20:
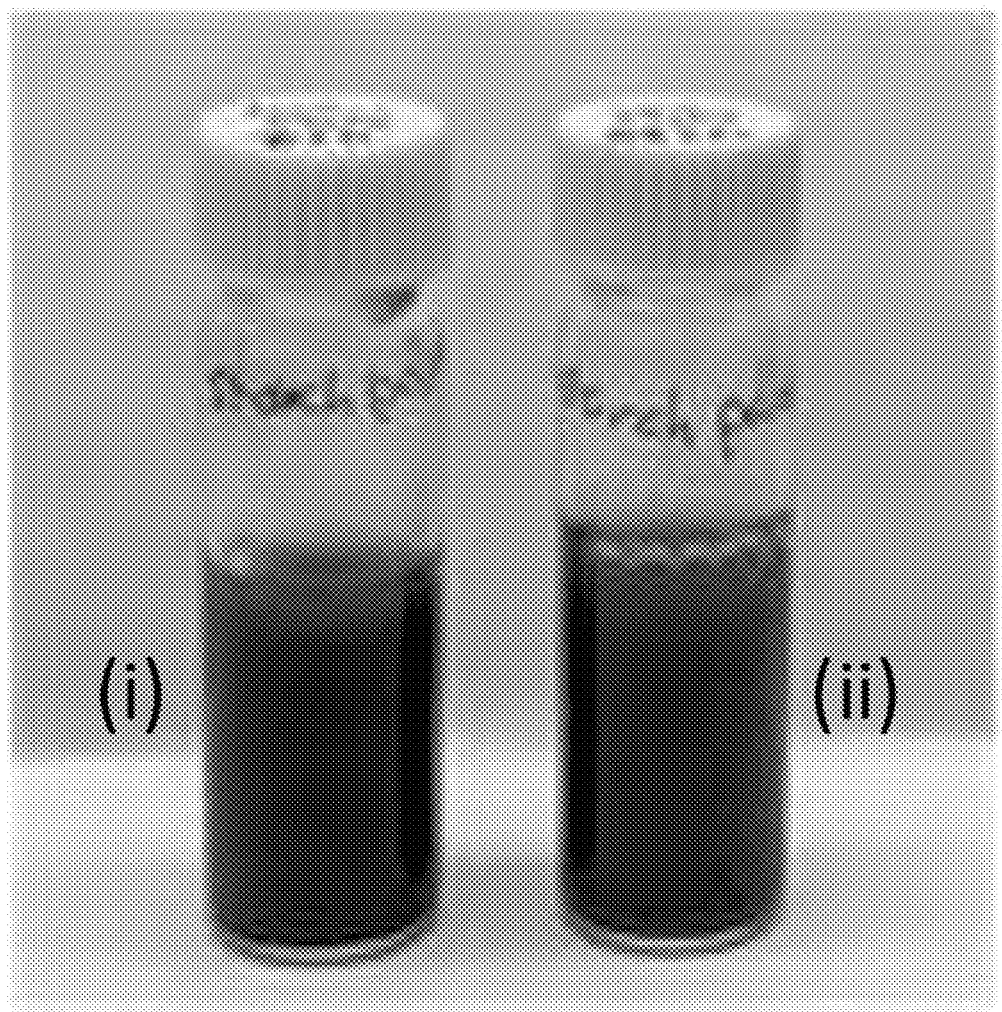
FIG. 20 shows an example photograph of the starch functionalized with FITC and RBITC with attached superparamagnetic $Fe_3O_4$ nanoparticles in suspension.
Figure 21:
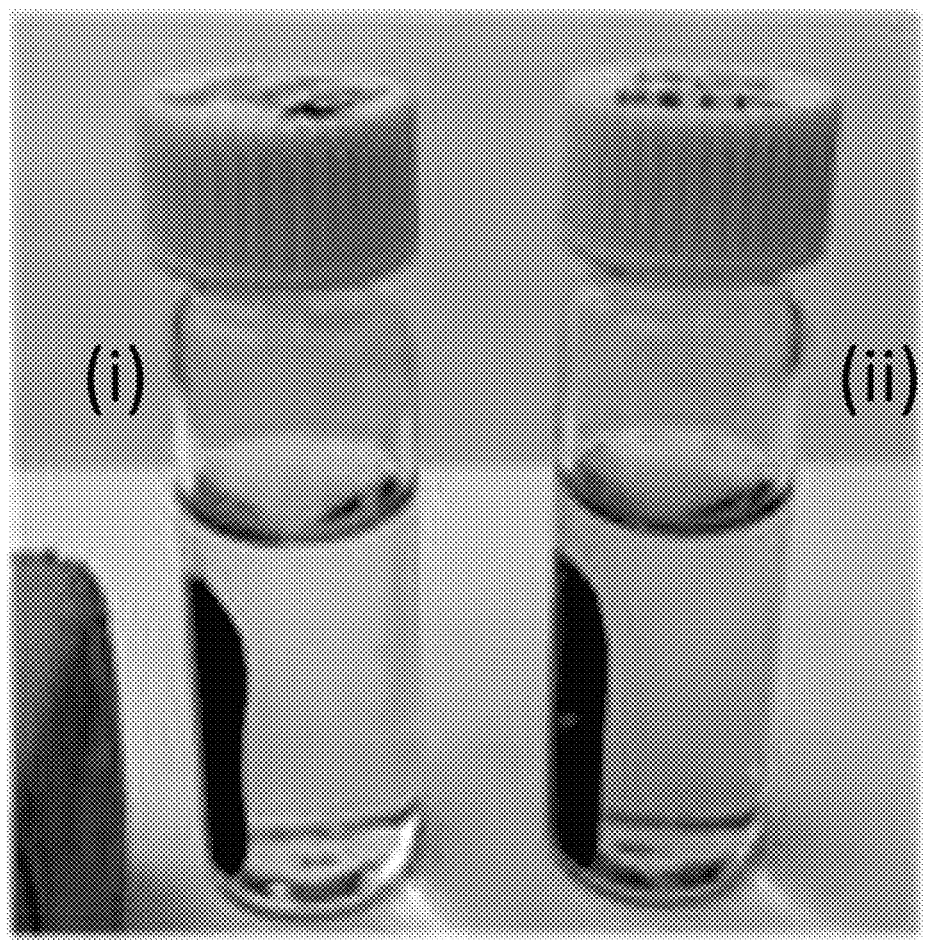
FIG. 21 shows an example photograph of the starch-dye-$Fe_3O_4$ complexes magnetically separated by an external magnet.
Figure 22:
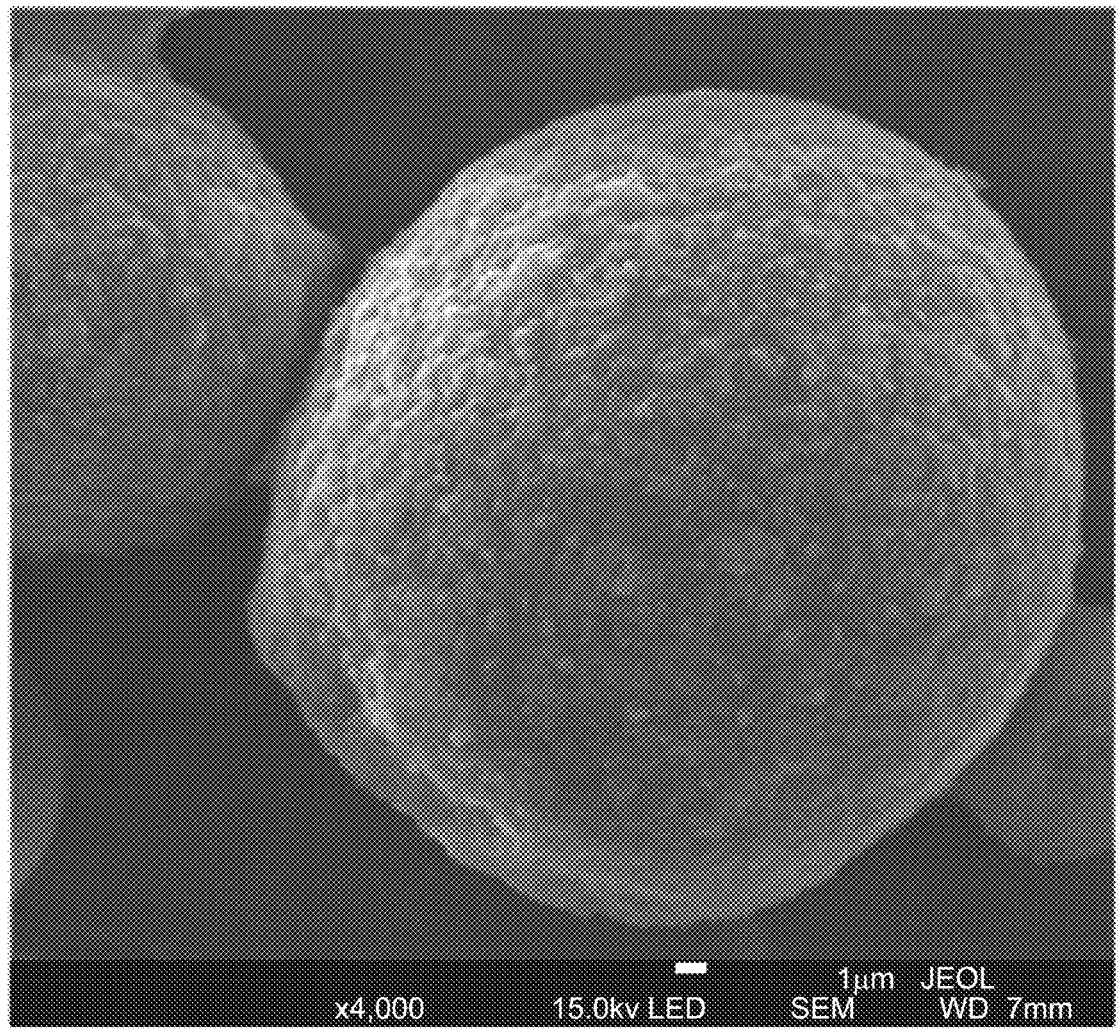
FIG. 22 shows an example SEM image of functionalized starch-RBITC with $Fe_3O_4$.

To incorporate SPIONs in the fluorescent starch, the above FITC or RBITC labeled starch (Example 5) was separated from reaction mixture and redispersed into 150 mL DI water. Next, 8.1 g of $FeCl_3.6H_2O$ and 4.2 g $FeSO_4.7H_2O$ were dissolved in the dispersion under $N_2$ atmosphere, followed by adding 7.5 mL of 29.5 wt % ammonia solution drop by drop at a rate of 2.5 mL/min with vigorous stirring. With the addition of ammonia solution, magnetite ($Fe_3O_4$) nanoparticles formed immediately, and the solution turns to black and viscous and then to deep brown and becomes more fluid. The reaction was allowed to continue at room temperature for 2 hours to ensure the formation of starch-dye-$Fe_3O_4$ composites. The starch-dye-$Fe_3O_4$ composite particles can be separated from solution by a magnet. The weight ratio of starch-dye to magnetic $Fe_3O_4$ in the composite is tunable as needed by changing relative ratio of the chemicals. FIG. 20 shows an example photograph of the starch functionalized with FITC (i) and RBITC (ii) with attached superparamagnetic $Fe_3O_4$ nanoparticles in suspension. FIG. 21 shows an example photograph of the starch-dye-$Fe_3O_4$ complexes (i) and (ii) magnetically separated by an external magnet. FIG. 22 shows an example SEM image of functionalized starch-RBITC with $Fe_3O_4$.

Example 7—Polystyrene Coating of SPION/Fluorescent Starch

Figure 23:
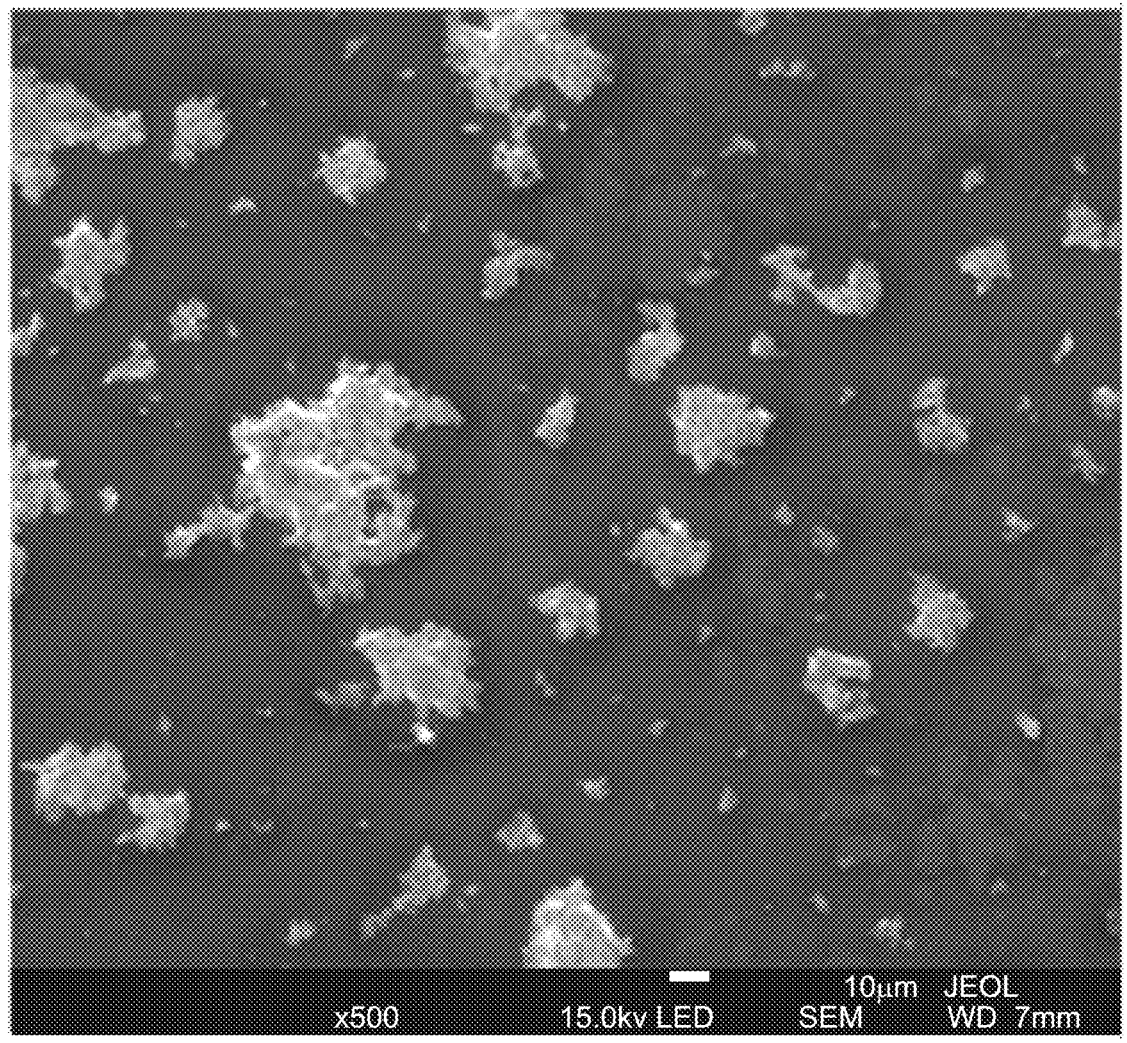
FIG. 23 shows an example SEM image of Starch-RBITC-$Fe_3O_4$ coated with polystyrene.

To form the polymer coated composite particles, the above collected starch-RBITC-$Fe_3O_4$ composite particles (from Example 6) were redispersed in 150 mL 0.25 wt % sodium dodecyl sulfate (SDS) solution and then 2.5 mL styrene was added. After stirring for 2 hours, 0.2 g ammonium persulfate was added to initiate the polymerization and the reaction was allowed to finish at 70° C. for 2 hours. The resulting starch-RBITC-$Fe_3O_4$—PS composite particles were separated and collected form solution by a magnet. FIG. 23 shows an example SEM image of Starch-RBITC-$Fe_3O_4$ coated with polystyrene.

Example 8—Fluorescence of Modified Starch

Figure 24:
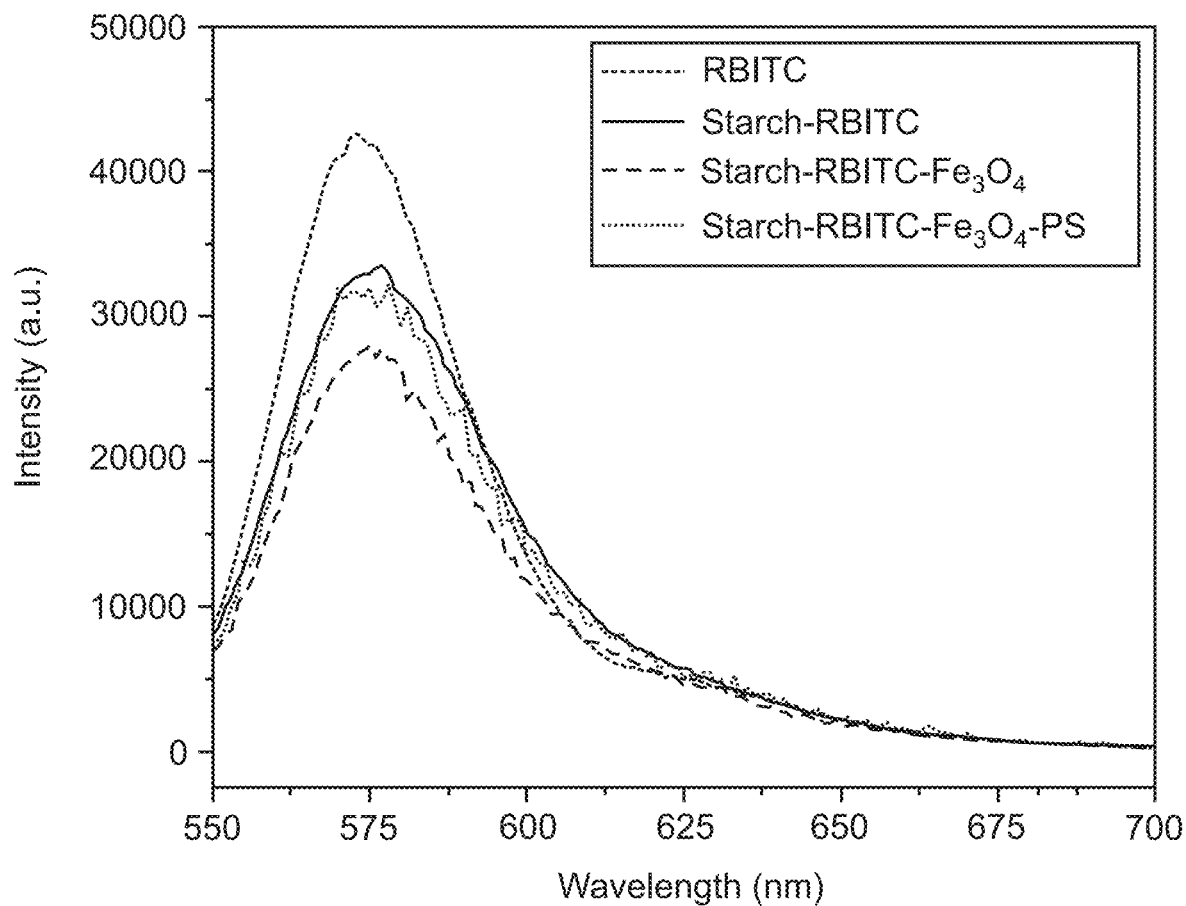
FIG. 24 shows an example fluorescence spectrum of RBITC, as well as modified starch polymers starch-RBITC, starch-RBITC-$Fe_3O_4$, and polystyrene-coated starch-RIBTC-$Fe_3O_4$—PS.

FIG. 24 shows an example fluorescence spectrum of RBITC, as well as modified starch polymers starch-RBITC, starch-RBITC-$Fe_3O_4$, and polystyrene-coated starch-RIBTC-$Fe_3O_4$—PS. As shown in FIG. 24, the inclusion of starch, $Fe_3O_4$, and polystyrene does not significantly alter the fluorescence signal of RBITC. Accordingly, the modified starch polymers can exhibit fluorescent signals and can be used as fluorescent tags in wellbore and subterranean applications. The spectra were measured with a Horiba NanoLog-3 fluorescence spectrometer, and the concentration of samples was approximately 1 wt % in water suspension.

The term "about" as used in this disclosure can allow for a degree of variability in a value or range, for example, within 10%, within 5%, or within 1% of a stated value or of a stated limit of a range.

The following units of measure have been mentioned in this disclosure:

| Unit of Measure | Full form |
|---|---|
| g | gram |
| mg | milligram |
| nm | nanometer |
| mL | milliliter |
| min | minute |
| kV | kilovolts |
| wt % | weight percent |

In some implementations, a nanoparticle tag includes a natural polysaccharide, a fluorescent dye, and superparamagnetic nanoparticles.

This aspect, taken alone or combinable with any other aspect, can include the following features. The natural polysaccharide includes at least one of chitosan, cellulose, starch, or alginate.

This aspect, taken alone or combinable with any other aspect, can include the following features. The fluorescent dye includes an isothiocyanate functional group.

This aspect, taken alone or combinable with any other aspect, can include the following features. The fluorescent dye is at least once of fluorescein isothiocyanate, rhodamine B isothiocyanate, or tetramethylrhodamine isothiocyanate.

This aspect, taken alone or combinable with any other aspect, can include the following features. The superparamagnetic nanoparticles include iron oxide.

This aspect, taken alone or combinable with any other aspect, can include the following features. The nanoparticle tag includes a polymer shell.

This aspect, taken alone or combinable with any other aspect, can include the following features. The polymer shell includes a polystyrene-based polymer.

This aspect, taken alone or combinable with any other aspect, can include the following features. The polystyrene-based polymer includes a derivative of styrene, p-methyl styrene, p-methoxy styrene, 2,4-dimethyl styrene, 2,4,6-trimethyl styrene, 4-chlorostyrene, or 4-bromostyrene, or any combination thereof.

This aspect, taken alone or combinable with any other aspect, can include the following features. The polymer shell includes a derivative of phenyl methacrylate, hexyl methacrylate, or butyl methacrylate, or any combination thereof.

This aspect, taken alone or combinable with any other aspect, can include the following features. The polymer shell encapsulates the natural polysaccharide, fluorescent dye, and superparamagnetic nanoparticles.

This aspect, taken alone or combinable with any other aspect, can include the following features. The polymer shell is dotted on the nanoparticle tag.

In some implementations, a method of making a nanoparticle tag includes functionalizing a natural polysaccharide with a fluorescent dye, and incorporating superparamagnetic nanoparticles into the nanoparticle tag.

This aspect, taken alone or combinable with any other aspect, can include the following features. The natural polysaccharide includes at least one of chitosan, cellulose, starch, or alginate.

This aspect, taken alone or combinable with any other aspect, can include the following features. The fluorescent dye includes an isothiocyanate functional group.

This aspect, taken alone or combinable with any other aspect, can include the following features. The fluorescent dye is at least once of fluorescein isothiocyanate, rhodamine B isothiocyanate, or tetramethylrhodamine isothiocyanate.

This aspect, taken alone or combinable with any other aspect, can include the following features. The superparamagnetic nanoparticles include iron oxide.

This aspect, taken alone or combinable with any other aspect, can include the following features. The method includes coating the nanoparticle tag with a polymer.

This aspect, taken alone or combinable with any other aspect, can include the following features. The polymer is a polystyrene-based polymer.

This aspect, taken alone or combinable with any other aspect, can include the following features. The polystyrene-based polymer includes a derivative of styrene, p-methyl styrene, p-methoxy styrene, 2,4-dimethyl styrene, 2,4,6-trimethyl styrene, 4-chlorostyrene, or 4-bromostyrene, or any combination thereof.

This aspect, taken alone or combinable with any other aspect, can include the following features. The polymer shell includes a derivative of phenyl methacrylate, hexyl methacrylate, or butyl methacrylate, or any combination thereof.

This aspect, taken alone or combinable with any other aspect, can include the following features. Coating the nanoparticle tag with a polymer includes fully encapsulating the nanoparticle tag with the polymer.

This aspect, taken alone or combinable with any other aspect, can include the following features. Coating the nanoparticle tag with a polymer includes dotting the nanoparticle tag with a polymer.

In some implementations, a method of determining the origin location of a subterranean rock sample includes mixing a nanoparticle tag into a fluid. The nanoparticle tag includes a natural polysaccharide core that includes a fluorescent dye and superparamagnetic nanoparticles. The method includes flowing the fluid through a work string into a subterranean formation, recovering subterranean rock samples from the subterranean formation, separating tagged rock samples from untagged rock samples using a magnet; and determining the origin location of the subterranean rock sample by analyzing the fluorescent signal of the nanoparticle tag.

This aspect, taken alone or combinable with any other aspect, can include the following features. The nanoparticle tag includes a polymer shell.

This aspect, taken alone or combinable with any other aspect, can include the following features. The method includes analyzing the polymer shell of the nanoparticle tag with mass spectroscopy.

This aspect, taken alone or combinable with any other aspect, can include the following features. Analyzing the polymer shell with mass spectroscopy includes analyzing the polymer shell with pyrolysis-gas chromatography-mass spectrometry.

This aspect, taken alone or combinable with any other aspect, can include the following features. Analyzing the polymer shell with mass spectroscopy includes analyzing the polymer shell with gas chromatography-flame ionization detection/mass spectrometry.

In some implementations, a method of tagging and tracing cut subterranean rock includes using a barcode mud tracer in a drilling fluid to tag a cut subterranean rock produced during drilling. The barcode mud tracer includes a nanoparticle tag. The nanoparticle tag includes a natural polysaccharide, a fluorescent dye, superparamagnetic nanoparticles, and a polymer coating. The method includes identifying the barcode mud tracer using two or more orthogonal analytical techniques.

The term "substantially" as used in this disclosure refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "solvent" as used in this disclosure refers to a liquid that can dissolve a solid, another liquid, or a gas to form a solution. Non-limiting examples of solvents are silicones, organic compounds, water, alcohols, ionic liquids, and supercritical fluids.

The term "room temperature" as used in this disclosure refers to a temperature of about 15 degrees Celsius (° C.) to about 28° C.

The term "downhole" as used in this disclosure refers to under the surface of the earth, such as a location within or fluidly connected to a wellbore.

As used in this disclosure, the term "drilling fluid" refers to fluids, slurries, or muds used in drilling operations downhole, such as during the formation of the wellbore.

As used in this disclosure, the term "fracturing fluid" refers to fluids or slurries used downhole during fracturing operations.

As used in this disclosure, the term "fluid" refers to liquids and gels, unless otherwise indicated.

As used in this disclosure, the term "subterranean material" or "subterranean zone" refers to any material under the surface of the earth, including under the surface of the bottom of the ocean. For example, a subterranean zone or material can be any section of a wellbore and any section of a subterranean petroleum- or water-producing formation or region in fluid contact with the wellbore. Placing a material in a subterranean zone can include contacting the material with any section of a wellbore or with any subterranean region in fluid contact the material. Subterranean materials can include any materials placed into the wellbore such as cement, drill shafts, liners, tubing, casing, or screens; placing a material in a subterranean zone can include contacting with such subterranean materials. In some examples, a subterranean zone or material can be any downhole region that can produce liquid or gaseous petroleum materials, water, or any downhole section in fluid contact with liquid or gaseous petroleum materials, or water. For example, a subterranean zone or material can be at least one of an area desired to be fractured, a fracture or an area surrounding a fracture, and a flow pathway or an area surrounding a flow pathway, in which a fracture or a flow pathway can be optionally fluidly connected to a subterranean petroleum- or water-producing region, directly or through one or more fractures or flow pathways.

As used in this disclosure, "treatment of a subterranean zone" can include any activity directed to extraction of water or petroleum materials from a subterranean petroleum- or water-producing formation or region, for example, including drilling, stimulation, hydraulic fracturing, clean-up, acidizing, completion, cementing, remedial treatment, abandonment, aquifer remediation, identifying oil rich regions via imaging techniques, and the like.

As used in this disclosure, a "flow pathway" downhole can include any suitable subterranean flow pathway through which two subterranean locations are in fluid connection. The flow pathway can be sufficient for petroleum or water to flow from one subterranean location to the wellbore or vice-versa. A flow pathway can include at least one of a hydraulic fracture, and a fluid connection across a screen, across gravel pack, across proppant, including across resin-bonded proppant or proppant deposited in a fracture, and across sand. A flow pathway can include a natural subterranean passageway through which fluids can flow. In some implementations, a flow pathway can be a water source and can include water. In some implementations, a flow pathway can be a petroleum source and can include petroleum. In some implementations, a flow pathway can be sufficient to divert water, a downhole fluid, or a produced hydrocarbon from a wellbore, fracture, or flow pathway connected to the pathway.

As used in this disclosure, "weight percent" (wt %) can be considered a mass fraction or a mass ratio of a substance to the total mixture or composition. Weight percent can be a weight-to-weight ratio or mass-to-mass ratio, unless indicated otherwise.

A number of implementations of the disclosure have been described.

Nevertheless, it will be understood that various modifications may be made without departing from the spirit and scope of the disclosure.

What is claimed is:

1. A nanoparticle tag, comprising:
a natural polysaccharide;
a fluorescent dye;

superparamagnetic nanoparticles; and
a polymer shell, wherein the polymer shell comprises a derivative of phenyl methacrylate, hexyl methacrylate, or butyl methacrylate, or any combination thereof, and wherein the polymer shell encapsulates the natural polysaccharide, the fluorescent dye, and the superparamagnetic nanoparticles.

2. The nanoparticle tag of claim 1, wherein the natural polysaccharide comprises at least one of chitosan, cellulose, starch, or alginate.

3. The nanoparticle tag of claim 1, wherein the fluorescent dye is derived from a precursor fluorescent dye, wherein the precursor fluorescent dye contains an isothiocyanate functional group.

4. The nanoparticle tag of claim 3, wherein the precursor fluorescent dye is at least once of fluorescein isothiocyanate, rhodamine B isothiocyanate, or tetramethylrhodamine isothiocyanate.

5. The nanoparticle tag of claim 1, wherein the superparamagnetic nanoparticles comprise iron oxide.

6. A method of making a nanoparticle tag, comprising:
forming a core of the nanoparticle tag, wherein the core comprises a natural polysaccharide;
functionalizing the natural polysaccharide with a fluorescent dye; and
incorporating superparamagnetic nanoparticles into the core of the nanoparticle tag; and
coating the core of the nanoparticle tag with a polymer shell, wherein the polymer shell comprises a derivative of phenyl methacrylate, hexyl methacrylate, or butyl methacrylate, or any combination thereof, and wherein coating the core of the nanoparticle tag with the polymer shell comprises fully encapsulating the core of the nanoparticle tag with the polymer shell.

7. The method of claim 6, wherein the natural polysaccharide comprises at least one of chitosan, cellulose, starch, or alginate.

8. The method of claim 6, wherein functionalizing the natural polysaccharide with the fluorescent dye comprises reacting the natural polysaccharide with a precursor fluorescent dye comprising an isothiocyanate functional group.

9. The method of claim 8, wherein the precursor fluorescent dye is at least once of fluorescein isothiocyanate, rhodamine B isothiocyanate, or tetramethylrhodamine isothiocyanate.

10. The method of claim 6, wherein the superparamagnetic nanoparticles comprise iron oxide.

11. A method of determining an origin location of a subterranean rock sample, comprising:
mixing a nanoparticle tag into a fluid, wherein the nanoparticle tag comprises a natural polysaccharide core that includes a fluorescent dye and superparamagnetic nanoparticles, and wherein the nanoparticle tag comprises a polymer shell, wherein the polymer shell comprises a derivative of phenyl methacrylate, hexyl methacrylate, or butyl methacrylate, or any combination thereof, and wherein the polymer shell encapsulates the natural polysaccharide, the fluorescent dye, and the superparamagnetic nanoparticles;
flowing the fluid through a work string into a subterranean formation;
recovering subterranean rock samples from the subterranean formation;
separating tagged rock samples from untagged rock samples using a magnet; and
determining the origin location of the subterranean rock sample by analyzing a fluorescent signal of the nanoparticle tag.

12. The method of claim 11, further comprising analyzing the polymer shell of the nanoparticle tag with mass spectrometry.

13. The method of claim 12, wherein analyzing the polymer shell with mass spectrometry comprises analyzing the polymer shell with pyrolysis-gas chromatography-mass spectrometry.

14. The method of claim 12, wherein analyzing the polymer shell with mass spectrometry comprises analyzing the polymer shell with gas chromatography-flame ionization detection/mass spectrometry.

15. A method of tagging and tracing cut subterranean rock, comprising:
using a barcode mud tracer in a drilling fluid to tag a cut subterranean rock produced during drilling, wherein the barcode mud tracer comprises a nanoparticle tag, wherein the nanoparticle tag comprises a natural polysaccharide, a fluorescent dye, superparamagnetic nanoparticles, and a polymer coating, wherein the polymer coating comprises a derivative of phenyl methacrylate, hexyl methacrylate, or butyl methacrylate or any combination thereof, and wherein the polymer coating encapsulates the natural polysaccharide, the fluorescent dye, and the superparamagnetic nanoparticles; and
identifying the barcode mud tracer using two or more orthogonal analytical techniques.

* * * * *